United States Patent [19]
Adams et al.

[11] Patent Number: 6,030,643
[45] Date of Patent: Feb. 29, 2000

[54] POTASSIUM, SODIUM AND TRIS OXAPROZIN SALT PHARMACEUTICAL FORMULATIONS

[75] Inventors: Mark E. Adams, Evergreen Park; Subhash Desai, Grayslake; Aziz Karim; Kalidas Paul, both of Skokie; Douglas J. Schaaf, Elgin; David J. Zold, Prospect Heights, all of Ill.

[73] Assignee: G.D. Searle & Co., Chicago, Ill.

[21] Appl. No.: 08/857,999

[22] Filed: May 16, 1997

Related U.S. Application Data

[60] Provisional application No. 60/019,033, May 20, 1996.

[51] Int. Cl.⁷ ........................................... A61K 9/20
[52] U.S. Cl. ..................... 424/464; 424/465; 514/777; 514/778; 514/781; 514/784; 514/886
[58] Field of Search ..................... 424/464, 465, 424/489; 514/374, 825, 886

[56] References Cited

U.S. PATENT DOCUMENTS

| | | | |
|---|---|---|---|
| 3,578,671 | 5/1971 | Woodley | 260/307 |
| 3,998,815 | 12/1976 | Bodor | 260/240 |
| 4,160,099 | 7/1979 | Bodor | 560/110 |
| 4,190,584 | 2/1980 | Weston | 548/236 |
| 4,385,049 | 5/1983 | Cuca | 424/167 |
| 4,465,838 | 8/1984 | Mughal | 548/236 |
| 4,532,253 | 7/1985 | Mughal | 514/374 |
| 4,599,359 | 7/1986 | Cooper | 514/557 |
| 5,059,626 | 10/1991 | Park | 514/658 |
| 5,350,769 | 9/1994 | Kasai | 514/567 |

FOREIGN PATENT DOCUMENTS

| | | | |
|---|---|---|---|
| 0 063 884 | 11/1982 | European Pat. Off. | C07D 263/32 |
| 0 274 870 A2 | 7/1988 | European Pat. Off. | A61K 9/10 |
| 37 00 158 A1 | 7/1987 | Germany | C07D 263/32 |
| 513232 | 6/1982 | Spain | C07D 263/32 |
| 1 206 403 | 9/1970 | United Kingdom | C07D 85/44 |
| 2 097 389 | 11/1982 | United Kingdom | C07D 263/32 |
| 2 148 894 | 6/1985 | United Kingdom | C07D 263/32 |
| WO 95/07079 | 3/1995 | WIPO | A61K 31/52 |
| WO 95/07103 | 3/1995 | WIPO | A61K 45/06 |

OTHER PUBLICATIONS

Copy of article entitled: "Searle's New Commitment to Market–Driven Science" from Searle Internal Magazine ("Circlet")—vol. 47, No. 23, Nov. 21, 1994.

*Primary Examiner*—James M. Spear
*Attorney, Agent, or Firm*—Fitzpatrick, Cella, Harper & Scinto

[57] ABSTRACT

Pharmaceutical compositions containing potassium, sodium or Tris salt of oxaprozin as an active agent. The pharmaceutical compositions of the present invention are useful in eliminating or ameliorating pain and in the treatment of inflammation and inflammation associated disorders such as rheumatoid arthritis and osteoarthritis.

36 Claims, No Drawings

POTASSIUM, SODIUM AND TRIS OXAPROZIN SALT PHARMACEUTICAL FORMULATIONS

This application claims the benefit under 35USC119(e) of Provisional Application 60/019,033 filed May 20, 1996.

BACKGROUND OF THE INVENTION

FIELD OF THE INVENTION

The present invention generally relates to novel pharmaceutical compositions or formulations containing a salt of oxaprozin for oral or other use, and to methods of treatment employing these formulations. These formulations contain only minor quantities of metallic stearates, such as the lubricants magnesium, calcium or zinc stearate, and only minor quantities of the binder methylcellulose. These formulations dissolve more rapidly, and result in a more rapid onset of the active oxaprozin salt agent than pharmaceutical formulations containing oxaprozin. Thus, these formulations are useful for the treatment of pain (as analgesic agents), as well as for the treatment of inflammation. More particularly, the present invention concerns pharmaceutical formulations containing potassium, sodium or Tris salts of oxaprozin in combination with a pharmaceutically-acceptable carrier, and methods of treating pain and inflammation employing these formulations.

Oxaprozin is a nonsteroidal antiinflammatory drug (NSAID) of the propionic acid class, chemically designated as 4,5-diphenyl-2-oxazolepropionic acid, which is currently being marketed in the United States by the pharmaceutical company G. D. Searle & Co., Skokie, Ill., under the trademark name DAYPRO®. The chemical formula for oxaprozin is:

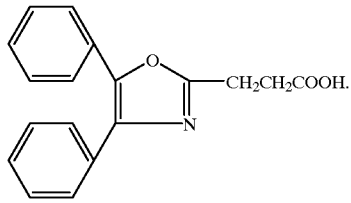

DAYPRO® tablets (oral caplets) contain 600 mg of oxaprozin as the active agent and have the following formulation:

| Ingredients | Mg/Tablet | % Composition |
| --- | --- | --- |
| Oxaprozin | 600.0 mg | 68.37% |
| Microcrystalline Cellulose PH-101, NF | 71.0 mg | 8.09% |
| Corn Starch, NF | 17.5 mg | 1.99% |
| Methylcellulose A15LVP, USP | 26.3 mg | 3.00% |
| Water, mg/Tab, %*Solids | 291.2 mg | 0% (Lost during drying) |
| Polacrilin Potassium IRP-88, NF | 26.3 mg | 3.00% |
| Microcrystalline Cellulose PH-102, NF | 126.0 mg | 14.36% |
| Magnesium Stearate, NF | 10.5 mg | 1.20% |
| Total | 877.6 mg | 100.00% |

In cases where a quick onset of action is important, the pharmacokinetics of oxaprozin allow therapy to be started with a one-time loading dose of 1200 to 1800 mg (not to exceed 26 mg/kg).

The potassium salt of oxaprozin has a solubility of 370 mg/ml, the TRIS salt of oxaprozin has a solubility of 380 mg/ml, and the sodium salt of oxaprozin has a solubility of 260 mg/ml compared to 1.7 mg/ml of oxaprozin. Thus, these salts of oxaprozin enable a faster dissolution and rate of absorption, leading to a more rapid onset of action and improved acute analgesic effects.

It was originally thought that the same formulation for oxaprozin which is currently marketed in the United States by G. D. Searle & Co. under the trademark name DAYPRO® could be employed for a potassium, sodium or Tris salt form of oxaprozin. However, it was discovered that tablets made from such formulation for the potassium salt of oxaprozin were deformed and would not disintegrate in water or dissolve in phosphate buffer media, with the result that little or no active agent was being released from these tablets during the first hour.

It is believed that the magnesium in the magnesium stearate (employed as a lubricant in the DAYPRO® formulation) was interacting with the potassium in tablets containing the potassium salt of oxaprozin and thereby forming a complex which produced an insoluble gel which prevented the tablets from disintegrating and dissolving.

It was subsequently determined that the magnesium stearate employed in the potassium, sodium and Tris oxaprozin salt formulations was not the only ingredient of these formulations which was adversely affecting the disintegration and dissolution of tablets containing these formulations. It is now theorized that disintegration and dissolution of these tablets was adversely affected by both the lubricant magnesium stearate and the binder methylcellulose.

It is desirable to develop pharmaceutical formulations of the present invention wherein about 75% of the active ingredient (potassium, sodium or TRIS salt of oxaprozin) becomes dissolved in phosphate buffer media within about 30 minutes. The most preferred pharmaceutical formulation has the characteristic that about 100% of the potassium salt of oxaprozin becomes dissolved in phosphate buffer media within 30 minutes. In comparison, when the potassium salt of oxaprozin was originally substituted for oxaprozin in the current DAYPRO® formulation, only about 23% of the potassium salt of oxaprozin became dissolved in phosphate buffer media within 30 minutes.

Because tablet formulations containing the potassium salt of oxaprozin dissolve more rapidly and the potassium salt of oxaprozin has a significantly higher solubility than oxaprozin, the tablet formulations containing the potassium salt of oxaprozin have a significantly more rapid onset of action of the active agent in comparison with DAYPRO®. As a result, tablet formulations containing a potassium salt of oxaprozin are useful as analgesic agents for the treatment of pain, as well as anti-inflammatory agents for the treatment of diseases such as rheumatoid arthritis and osteoarthritis.

SUMMARY OF THE INVENTION

The present invention provides a pharmaceutical formulation for oral administration which is pharmaceutically acceptable, and which produces a desired therapeutic response, in tablet, caplet or other compressed form which comprises the potassium, sodium or Tris salt of oxaprozin.

The present invention also provides a pharmaceutical formulation for oral administration which is pharmaceutically acceptable, and which produces a therapeutic response, in tablet, caplet or other compressed form which comprises:

(a) the potassium, sodium or Tris salt of oxaprozin as the active ingredient; and (b) a suitable lubricant.

The present invention further provides a pharmaceutical formulation for oral administration which is pharmaceutically acceptable, and which produces a therapeutic response, in tablet, caplet or other compressed form which comprises: (a) the potassium, sodium or Tris salt of oxaprozin as the active ingredient; (b) a suitable lubricant; and (c) a suitable binder.

The present invention still further provides a method for eliminating or ameliorating pain in an animal, and methods for treating inflammation and inflammation-associated disorders, such as rheumatoid arthritis and osteoarthritis, and related disorders and conditions, in an animal, comprising administering a pharmaceutical formulation of the present invention, as described herein, to the animal.

The pharmaceutical formulations of the present invention may contain minor quantities of metallic stearates (less than 0.976% of the total percentage weight of a tablet or other compressed form containing such a formulation), such as the lubricants, magnesium, calcium and zinc stearate, in order to prevent any deleterious effect upon the disintegration and/or dissolution of tablets, caplets or other pressed forms of these formulations. Preferably, the pharmaceutical formulations of the present invention do not contain any metallic stearates.

The pharmaceutical formulations of the present invention may contain minor quantities of the binder methylcellulose (less than 2% of the total percentage weight of a tablet containing such a formulation) in order to prevent any deleterious effect upon the disintegration and/or dissolution of tablets, caplets or other pressed forms of these formulations. Preferably, the pharmaceutical formulations of the present invention do not contain any methylcellulose.

DETAILED DESCRIPTION OF THE INVENTION (1) Definitions

For purposes of clarity, the terms and phrases used throughout this specification and the appended claims are defined in the manner set forth directly below.

The term "analgesia" as used herein means the reduction, or absence, of sensibility to pain, designating particularly the relief of pain without loss of consciousness.

The term "animal" as used herein includes mammals and nonmammals, and further includes humans and non-human mammals.

The abbreviation "AUC" as used herein means area under the curve, which is a predictor of the extent of absorption of a compound in the body.

The abbreviations "AUC o-∞", "AUC (O-Infinity)" and "AUC (O-Inf.)" as used herein mean area under the plasma concentration time curve between time points zero hours and infinity.

The abbreviation "$C_{max}$" as used herein means peak plasma concentration.

The term "composition" as used herein means a product which results from the combining of more than one ingredient.

The abbreviation "Conc" as used herein means concentration.

The abbreviation "CV" as used herein means coefficient of variation, and is a function of the standard error of the mean. It indicates the variability of a test, and is calculated by dividing the standard error (SE) by the mean concentration measured, and multiplying by 100%.

The abbreviation "DMF" as used herein means dimethylformamide.

The abbreviation "DMSO" as used herein means dimethyl sulfoxide.

The abbreviation "DSC" as used herein means Differential Scanning Calorimetry.

The phrase "$EC_{50}$ concentration" as used herein means that concentration of a compound or drug which is necessary to elicit a 50% maximal biological response.

The phrase "$ED_{50}$ dose" as used herein means that dose of a compound or drug which produced a biological effect, such as producing analgesia, in 50% of the animals to which the compound or drug was administered.

The abbreviation "Form. No." as used herein means Formulation Number.

The abbreviation "HPLC" as used herein means High Pressure Liquid Chromatography.

The terms "K-mole" and "kilomole" as used herein means one thousand moles.

The abbreviation "LCL" as used herein means lower confidence level.

The abbreviations "Min" or "min" as used herein mean minutes.

The abbreviation "MPLC" as used herein means Medium Pressure Liquid Chromatography.

The abbreviation "MRT" as used herein means mean retention time, and measures the length of time a compound remains in the body.

The abbreviation "n" or "N" as used herein in relationship to data means the number of items or patients tested in a particular experiment.

The abbreviation "NF" as used herein means National Formulary Specifications.

The term "oxaprozin" as used herein means 4,5-diphenyl-2-oxazolepropionic acid, which has the following chemical structure:

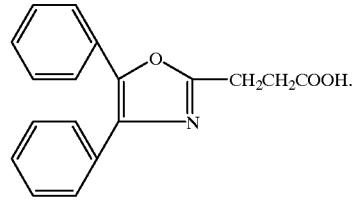

The abbreviation "%CD" as used herein means % colloidal silicon dioxide.

The abbreviation "%CS" as used herein means % corn starch.

The abbreviation "%K OXA" as used herein means % potassium oxaprozin.

The abbreviation "%MC" as used herein means % microcrystalline cellulose.

The abbreviation "%SA" as used herein means % stearic acid.

The phrase "pharmaceutically acceptable" is employed herein to refer to those compounds, materials, compositions, and/or dosage forms which are, within the scope of sound medical judgment, suitable for use in contact with the tissues of animals without excessive toxicity, irritation, allergic response, or other problem or complication, commensurate with a reasonable benefit/risk ratio.

The phrases "potassium oxaprozin" and "potassium salt of oxaprozin" as used herein mean 4,5-diphenyl-2-oxazolepropanoic acid, potassium salt, which has the following chemical structure:

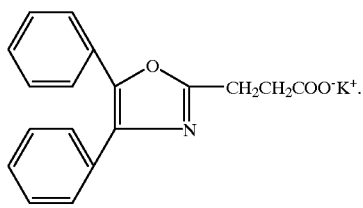

The abbreviation "QD" as used herein means once daily.

The abbreviations "RPM" or "rpm" as used herein means rotations per minute.

The abbreviation "RSD" as used herein means the percent of relative standard deviation, which is variation within a population relative to the mean of the same population.

The abbreviation "SD" or "StdDev" as used herein means standard deviation of the mean.

The abbreviations "SEM" and "$S_{\bar{x}}$" as used herein mean the standard error of the mean, and are calculated as follows:

$$S_{\bar{x}} = \frac{S}{\sqrt{N}},$$

where S is standard deviation and N is number of samples.

The phrases "sodium oxaprozin" and "sodium salt of oxaprozin" as used herein mean 4,5-diphenyl-2-oxazolepropanoic acid, sodium salt, which has the following chemical structure:

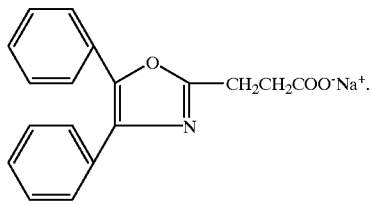

The phrase "therapeutically-effective amount" as used herein means an amount of a compound, material, or composition which is an effective dose for eliminating or ameliorating pain in an animal, for eliminating or reducing inflammation in an animal, or for producing some other desired therapeutic effect, at a reasonable benefit/risk ratio applicable to any medical treatment.

The abbreviation "$T_{max}$" as used herein means time of maximum concentration in the plasma, and is an observed value derived by determining the time that the maximum plasma concentration is obtained, as is known by those of skill in the art.

The abbreviations "$T_{1/2}$" and "$t_{1/2}\beta$" as used herein mean the half-life of a compound.

The term "TRIS" as used herein means tris(hydroxymethyl)aminomethane, which has the following chemical structure:

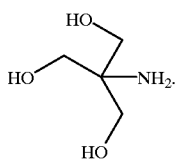

The phrases "Tris oxaprozin" and "Tris salt of oxaprozin" as used herein mean 4,5-diphenyl-2-oxazolepropanoic acid, tris(hydroxymethyl)aminomethane salt, which has the following chemical structure:

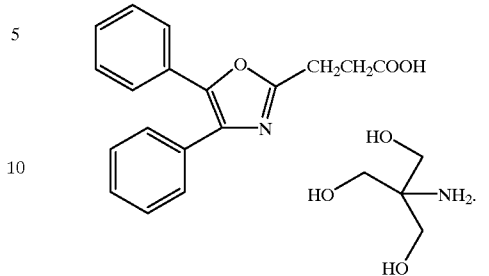

The abbreviation "UCL" as used herein means upper confidence level.

The abbreviation "USP" as used herein means U.S. Pharmacopia.

(2) Description of Invention

In one aspect, the present invention provides a pharmaceutical formulation for oral administration which is pharmaceutically acceptable, and which produces a therapeutic response, in tablet, caplet or other compressed form which comprises the potassium, sodium or Tris salt of oxaprozin.

In a further aspect, the present invention provides a pharmaceutical formulation for oral administration which is pharmaceutically acceptable, and which produces a therapeutic response, in tablet, caplet or other compressed form which comprises: (a) the potassium, sodium or Tris salt of oxaprozin as the active ingredient; and (b) a suitable lubricant.

In another aspect, the present invention provides a pharmaceutical formulation for oral administration which is pharmaceutically acceptable, and which produces a therapeutic response, in tablet, caplet or other compressed form which comprises: (a) the potassium, sodium or Tris salt of oxaprozin as the active ingredient; (b) a suitable lubricant; and (c) a suitable binder.

In yet a further aspect, the present invention provides a method for eliminating or ameliorating pain in an animal, and methods for treating inflammation and inflammation-associated disorders, such as rheumatoid arthritis and osteoarthritis, and related disorders and conditions, in an animal, comprising administering a pharmaceutical formulation of the present invention, as described herein, to the animal.

The pharmaceutical compositions of the present invention may be specially formulated for oral administration in solid dosage form, such as a tablet, caplet or any other compressed form.

The pharmaceutical formulations of the present invention may contain minor quantities of metallic stearates (less than 0.976% of the total percentage weight of a tablet or other compressed form containing such a formulation), such as the lubricants magnesium, calcium and zinc stearate, in order to prevent any deleterious effect upon the disintegration and/or dissolution of tablets, caplets or other pressed forms of these formulations. Preferably, the pharmaceutical formulations of the present invention do not contain any metallic stearates. If the pharmaceutical formulations of the invention contain a metallic stearate, the percentage weight of the metallic stearate should be less than 0.976% of the total weight of a tablet or other compressed form of the pharmaceutical formulation, and more preferably should not be greater than 0.5% of the total.

The pharmaceutical formulations of the present invention may contain minor quantities (less than 2% of the total percentage weight of a tablet containing such a formulation) of the binder methylcellulose in order to prevent any deleterious effect upon the disintegration and/or dissolution of tablets, caplets or other pressed forms of these formulations. At percentages greater than this, the methylcellulose forms a gel on the tablet which is visible, and which prevents the tablet from dissolving. Preferably, the pharmaceutical formulations of the present invention do not contain any methylcellulose.

Formulations of the invention suitable for oral administration may be in the form of pills, tablets, caplets, or other compressed forms, each containing a predetermined amount of active ingredient.

The pharmaceutical formulation of the present invention (pills, tablets, caplets and the like) may have the active ingredient (the potassium, sodium or Tris salt of oxaprozin) optionally mixed with one or more pharmaceutically-acceptable carriers, such as sodium citrate or dicalcium phosphate, and/or with any of the following excipients: (1) fillers or extenders, such as starches, lactose, sucrose, glucose, mannitol, and/or silicic acid; (2) binders, such as carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, small quantities of magnesium stearate, calcium stearate, zinc stearate, solid polyethylene glycols, sodium lauryl sulfate, and mixtures thereof; (10) glidants, such as colloidal silicon dioxide; (11) anti-adherents, such as colloidal silicon dioxide; (12) coloring agents, such as food, drug and cosmetic yellow #6; (13) buffering agents, such as calcium carbonate; (14) emulsifiers, such as Tween 40; (15) release agents, such as calcium acetate phthalate; (16) coating agents, such as hydroxypropyl methylcellulose and Opadry® Blue; (17) sweetening agents, such as sugar; (18) flavoring agents, such as peppermint or spearmint; (20) preservatives, such as butylated hydroxy anisol; (21) antioxidants, such as ascorbic acid or ethylenediamine tetraacetate; (22) granulating agents, such as methylcellulose; and (23) surfactants, such as polyoxyl 40 stearate, sodium lauryl sulfate, and other like ingredients.

The most preferred pharmaceutical formulation of the present invention is the following potassium salt oxaprozin tablet formulation:

Most Preferred Formulation -
Oxaprozin Potassium Salt Tablet Formulation
(600 Milligram Tablet Formation)

| Ingredient- Core Tablet | Amount (mg/Tablet) | Amount (Kg/370.0 kg Batch) | Percent of the Total |
|---|---|---|---|
| Potassium Salt of Oxaprozin (Active Agent) | 677.9[1] mg | 305.9 kg | 82.67% |
| Microcrystalline Cellulose NF (Filler) | 104.4 mg | 47.1 kg | 12.73% |
| Pregelatinized Corn Starch NF (Binder) | 17.7 mg | 8.0 kg | 2.16% |
| Stearic Acid NF | 16.0 mg | 7.2 kg | 1.95% |

-continued

Most Preferred Formulation -
Oxaprozin Potassium Salt Tablet Formulation
(600 Milligram Tablet Formation)

| (Lubricant) Colloidal Silicon Dioxide NF (Glidant) | 4.0 mg | 1.8 kg | 0.49% |
|---|---|---|---|
| Purified Water USP | — | 67.0[2] kg | 0% |
| Total: (Tablet Core Weight) | 820.0 mg | 437.0 kg | 100% |

| Ingredient- Film Coat | Amount (mg/Tablet) | Amount (Kg/370.0 kg Batch) | Percent of the Total |
|---|---|---|---|
| Opadry® Blue YS-1-10682 | 24.0 mg | 8.37 kg | 2.84% |
| Purified Water USP | — | 56.02[2] kg | 0% |
| Total: (Film-Coated Tablet Weight) | 844.0 mg | 8.37 kg | 100% |

[1]Equivalent to 600 mg of oxaprozin.
[2]Removed during processing.

The pharmaceutical compositions of the present invention may also be used in the form of veterinary formulations.

COMPONENTS OF THE PHARMACEUTICAL FORMULATIONS OF THE INVENTION AND RANGES THEREOF

Active Agent

The active agent component (potassium, sodium or Tris salt of oxaprozin) of the pharmaceutical formulations of the present invention is the ingredient which gives the desired therapeutic response, such as pain relief, when administered to a patient. If an insufficient amount of active agent is present in these formulations, the desired therapeutic response will not be obtained. If, on the other hand, too much active agent is present in these formulations, the therapeutic response may be too great, or this may result in one or more undesirable side effects. Thus, the pharmaceutical formulations of the present invention contain a sufficient amount of active agent to produce a desired therapeutic response in a patient, such as pain relief or a decrease in inflammation, but an amount which is less than that which would result in too great of a response and/or would cause one or more undesirable side effects.

The percent range of the total tablet weight of the active agent which is preferably employed in the pharmaceutical formulations of the present invention is from about 37.14% to about 100%, more preferably from about 60% to about 99.75%, still more preferably from about 70% to about 90%, and most preferably from about 80% to about 86%.

Binders

The binder component of some of the pharmaceutical formulations of the present invention aids tablets or other compressible forms of these formulations to be formed by a mechanical tablet press. Without the binder, the active agent would not as easily take the form of a stable tablet, caplet or other compressed form. If an insufficient amount of binder is employed in these formulations, a compressible granulation in a large (commercial) scale may not be formed. If, on the other hand, too much binder is employed, the resulting tablets may be too hard and, thus, may not disintegrate and/or dissolve properly within a specified time. Thus, the pharmaceutical formulations of the invention which contain a binder contain a sufficient amount of binder to form a compressible granulation in a large (commercial) scale, but an amount which is less than that which would result in tablets or other compressible forms which are too hard and, thus, which do not disintegrate or dissolve properly within a specified time.

Group I POLYMERIC BINDERS
    SOLLUBLE NON-CELLULOSIC BINDERS IE. polyvinylpyrrolodone, polyvinyl alcohol
    CELLULOSIC BINDERS IE. methylcellulose, hydroxypropyl meythlcellulose carboxymethylcellulose, etc.
Group II POLYSACCHARIDES
    NATURAL GUMS IE. acacia, sodium alginate, tragacanth, locust bean gum, guargum, pectin, detarium micrcarpium gum, macrogol stearate, baobob fruit, etc.
    SUGARS & STARCHES IE. sucrose, fructose, dextrose, pregelatinized corn starch, metastable amylose, amylodextrin, maltodextrin, cyclodextrins, xylans, etc.
Group III POLYOLS
    IE. glycerine, sorbitol, mannitol, xytol, etc.
Group IV PROTEINS
    IE. gelatin, cassien, etc.

In investigating the polymeric binders, polyvinylpyrrolidone appears to have no limit for use and as much of the excipient as can be practicably used in making a tablet of realistic size can be used. Polyvinyl alcohol appears to have an upper limit of use at 20% w/w. Dissolution results are provided below:

| | 10 MIN | 15 MIN | 20 MIN | 30 MIN | 45 MIN | 60 MIN |
|---|---|---|---|---|---|---|
| Formula containing 30% w/w polyvinylpyrrolidone | | | | | | |
| Concentration | 42.3 | 57.3 | 68.9 | 85.4 | 96.3 | 96.9 |
| Standard Deviation | 1.1 | 1.5 | 1.7 | 1.6 | 1.0 | 0.4 |
| Formula containing 20% w/w polyvinyl alcohol | | | | | | |
| Concentration | 37.0 | 49.2 | 60.0 | 77.9 | 93.5 | 98.1 |
| Standard Deviation | 2.8 | 3.6 | 3.6 | 4.2 | 2.7 | 0.8 |

The conclusion that can be drawn for soluble non-cellulosic binders is that they are effective up to maximum limits of use of 20 to 30% w/w in potassium oxaprozin formulas. For the cellulosic polymeric binders, hydroxypropyl methylcellulose was chosen to represent this class and the upper limit was defined by the following dissolutions:

| | 10 MIN | 15 MIN | 20 MIN | 30 MIN | 45 MIN | 60 MIN |
|---|---|---|---|---|---|---|
| Formula containing 17.5% w/w hydroxypropyl methylcellulose | | | | | | |
| Concentration | 37.1 | 50.1 | 62.0 | 79.4 | 91.7 | 96.6 |
| Standard Deviation | 1.2 | 1.6 | 2.1 | 3.6 | 2.7 | 1.0 |
| Formula containing 20% w/w hydroxypropyl methylcellulose | | | | | | |
| Concentration | 27.0 | 40.9 | 50.9 | 67.8 | 82.5 | 90.7 |
| Standard Deviation | 11.8 | 4.2 | 4.2 | 6.9 | 5.1 | 5.6 |

The upper limit for use of the cellulosic binders is between 17.5 and 20% w/w.

Acacia was chosen to be representative of a typical natural gum. The dissolution results are shown below:

| | 10 MIN | 15 MIN | 20 MIN | 30 MIN | 45 MIN | 60 MIN |
|---|---|---|---|---|---|---|
| Formula containing 17.5% w/w acacia | | | | | | |
| Concentration | 37.3 | 50.8 | 62.3 | 79.5 | 94.6 | 98.8 |
| Standard Deviation | 1.5 | 1.5 | 1.8 | 2.0 | 1.4 | 0.5 |
| Formula containing 20% w/w acacia | | | | | | |
| Concentration | 31.7 | 43.7 | 54.4 | 71.4 | 89.3 | 98.7 |
| Standard Deviation | 1.7 | 2.8 | 3.2 | 2.8 | 2.0 | 0.9 |

The results indicate that natural gum binders will be effective up to 17.5 to 20% w/w, but not beyond that range.

Data has been generated for two excipients from the sugars and starches group. Pregelatinized corn starch was covered within the base patent. Product could be made that met requirements at the 30% w/w level. Sucrose was also studied. The excipient was very effective when prepared at a 3.9% w/w level using wet granulation.

30% w/w sucrose was attempted using wet granulation, the wet granulation congealed in the oven during drying. Tablets containing 30% w/w were prepared adding the sucrose dry. Very soft tablets resulted (0.9–2.4 Kp) These tablets were submitted for dissolution, due to the logic that combining the two processes would give acceptable tablets up to 30% and above. The dissolution results for the 30% dry binder tablets are provided below:

| Formula containing 30% w/w sucrose | | | | | | |
|---|---|---|---|---|---|---|
| | 10 MIN | 15 MIN | 20 MIN | 30 MIN | 45 MIN | 60 MIN |
| Concentration | 84.8 | 99.5 | 100.7 | 100.8 | 100.8 | 100.8 |
| Standard Deviation | 2.8 | 2.6 | 3.2 | 3.2 | 3.2 | 3.3 |

The results for pregelatinized starch and sucrose indicate for sugars and starches no maximum limit for use exists and as much of the excipient as can be practicably used in making a tablet of realistic size can be used.

Glycerine was chosen as the polyol to study. The limiting factor for functionality of this excipient was not dissolution. Sticking began to occur above 20% w/w. Between 25 and 30% addition a paste begins to occur from just the addition of the glycerine. At 30% the paste was dried and milled. Tablets were made by rotating the press by hand. This was to note if sticking could be overcome, if there would be an upper limit based on dissolution. The results for both 20% and 30% are reported below.

| | 10 MIN | 15 MIN | 20 MIN | 30 MIN | 45 MIN | 60 MIN |
|---|---|---|---|---|---|---|
| Formula containing 20% w/w glycerine | | | | | | |
| Concentration | 91.2 | 103.1 | 102.5 | 103.0 | 102.4 | 102.6 |
| Standard Deviation | 2.2 | 2.6 | 0.6 | 1.7 | 0.7 | 0.7 |
| Formula containing 30% w/w glycerine | | | | | | |
| Concentration | 89.0 | 101.0 | 101.5 | 101.5 | 101.5 | 101.5 |
| Standard Deviation | 1.7 | 0.9 | 0.8 | 0.8 | 0.8 | 0.8 |

The conclusion for the polyols is that if sticking can be overcome, there is no limit to the % level that can practicably be used in the formulation. If not, than the upper limit is between 20 and 25%.

In studying the protein binders, the upper limit is determined by the quantity of solvent that can be transferred to the drug substrate and still be able to make a granulation. The reason is that protein binders need to be hydrated to function as a binder. Gelatin was studied and the upper limit was observed to be 5%. The result was acceptable and is given below.

| Formula containing 5% w/w gelatin | | | | | | |
|---|---|---|---|---|---|---|
| | 10 MIN | 15 MIN | 20 MIN | 30 MIN | 45 MIN | 60 MIN |
| Concentration | 61.2 | 79.7 | 92.1 | 99.7 | 99.6 | 99.7 |
| Standard Deviation | 1.5 | 1.4 | 1.1 | 0.6 | 0.6 | 0.5 |

The conclusion is that protein type binders can be used up to 5% in the formula.

Binders, and the percent ranges thereof of the total tablet weight, which may be employed in the formulations of the present invention include cornstarch USP (preferably from about 0% to about 10%), pregelatinized cornstarch (preferably from about 0% to about 99%, more preferably 0.25–30% and most preferably 0.5–5%), sucrose (preferably from about 0% to about 85%), polyvinylpyrrolidone (preferably from about 0% to about 20%), methylcellulose (various viscosity grades) (preferably from about 0% to about 2%), sodium carboxymethyl cellulose (low viscosity grade) (preferably from about 0% to about 2%), and ethylcellulose (various viscosity grades) (preferably from about 0% to about 2%).

Lubricants

The lubricant component of some of the pharmaceutical formulations of the present invention aids a tablet or other compressible form which has been formed in a mechanical press in its ability to be ejected from the press without breaking. If too little lubricant is employed in these formulations, the resulting formulation may not release from the press properly, and the result may be broken tablets or a damaged tablet press. If, on the other hand, too much lubricant is employed in these formulations, it can adversely affect the way the tablet disintegrates and/or dissolves and, thus, decrease the effect of the active agent. It can also inhibit the binding of the formulations in a mechanical press, so that the capability of compressing a tablet is diminished. Thus, the formulations of the present invention which contain a lubricant contain a sufficient amount of lubricant to allow a tablet or other compressible form of the formulations to be ejected from a mechanical press without breaking, but an amount which is less than that which would adversely affect the way the tablet disintegrates and/or dissolves, or which would inhibit the binding of the formulations.

Generally, water-insoluble lubricants are more preferred for use in the present invention than water-soluble lubricants because the former are generally more effective as lubricants.

A partial list of insoluble (or slowly soluble) lubricants includes the following: stearic acid, sodium stearate, potassium stearate, calcium stearate, magnesium stearate, zinc stearate, talc, polyethylene glycol 6000, glyceryl behenate, etc.

Stearic acid was studied and is reported herein and the maximum level of use based on dissolution was found to be between 17.5 and 20%. Magnesium stearate was also studied as reported herein and found to have a maximum level of less than 1%. Magnesium stearate is an insoluble lubricant and the magnesium ion is known to form an insoluble precipitate with the drug. Stearic acid could be thought of as a slowly soluble lubricant. Sodium stearate and potassium stearate are also slowly soluble ingredients. Calcium stearate, zinc stearate, talc, polyethylene glycol 6000 and glyceryl behenate are all insoluble. Sodium Stearate was chosen as another slowly soluble candidate for study and talc and calcium stearate were chosen as insoluble candidates for study.

Sodium Stearate tablets with excellent appearance and hardness were prepared. Dissolution was the only limiting criteria and the maximum level for use of this material was found to be 20%.

| Formula containing 20% w/w sodium stearate | | | | | | |
|---|---|---|---|---|---|---|
| | 10 MIN | 15 MIN | 20 MIN | 30 MIN | 45 MIN | 60 MIN |
| Concentration | 34.3 | 45.7 | 56.9 | 75.2 | 89.8 | 95.2 |
| Standard Deviation | 8.5 | 14.6 | 18.8 | 22.7 | 18.4 | 13.8 |

The upper limits for talc and calcium stearate were found to be 15% w/w and 5% w/w respectively. The limiting factors were found to be compressibility. The hardness range for the tablets made with talc was 2.5 to 7.0 Kp and for tablets containing calcium stearate were 2.9 to 4.6 Kp. The dissolution data obtained was as follows:

| | 10 MIN | 15 MIN | 20 MIN | 30 MIN | 45 MIN | 60 MIN |
|---|---|---|---|---|---|---|
| Formula containing 15% w/w talc | | | | | | |
| Concentration | 59.8 | 81.0 | 91.9 | 96.2 | 97.5 | 98.1 |
| Standard Deviation | 3.2 | 3.6 | 5.3 | 3.6 | 2.5 | 2.0 |
| Formula containing 5% w/w calcium stearate | | | | | | |
| Concentration | 49.2 | 67.3 | 80.8 | 96.4 | 98.4 | 98.3 |
| Standard Deviation | 2.7 | 3.3 | 3.3 | 1.2 | 0.6 | 0.7 |

The conclusion that can be drawn for the slowly soluble materials, IE. stearic acid, sodium and potassium stearates is that dissolution is the limiting factor and that up to 17.5 to 20% w/w, these materials function well as lubricants. The conclusions that can be drawn for the insoluble stearates is that calcium stearate functions differently than magnesium stearate. For magnesium stearate the limiting factor is dissolution. For calcium stearate, compressibility becomes the limiting factor. It can be assumed that zinc stearate will act similarly to the calcium stearate and that these two materials have an upper limit of less than 5% in the formula. The other insoluble lubricants should act similar to talc with compressibility becoming an issue before dissolution with the upper limit being 15%. Compressibility drops off much quicker for insoluble lubricants than for soluble lubricants. Comparable hardnesses were possible at 30% for sodium lauryl sulfate and sodium steryl fumerate to what was seen at 15% for talc and 5% for calcium stearate With the exceptions of hydrogenated castor oil and glycerol behenate, any water-insoluble lubricant may be employed in the pharmaceutical formulations of the present invention. Water-insoluble lubricants, and the percent ranges thereof of the total tablet weight, which may be employed in the formulations of the present invention include magnesium, calcium and zinc stearate (less than 0.976%, preferably from about 0% to about 0.25%, most preferably 0%), stearic acid (preferably from about 0% to about 17.5%, more preferably from about 1% to about 4%, most preferably from about 1% to about 2%), hydrogenated vegetable oil (preferably from about 0% to about 5%, more preferably from about 0.25% to about 2%), talc (preferably from about 0% to about 10%, more preferably from about 1% to about 5%).

There are many soluble lubricants. The following is a partial list: boric acid, sodium benzoate, sodium acetate, sodium chloride, potassium chloride, DL-leucine HCl, carbowax-4000, sodium oleate, sodium lauryl sulfate, magnesium lauryl sulfate, glyceryl palmitate stearate, PEG behenate, sodium stearyl fumerate, sodium stearyl lactylate, etc. Three of these were picked to represent the others: sodium chloride, sodium lauryl sulfate, and sodium stearyl fumerate. All three were found to give acceptable dissolution profiles at a 30% w/w level in the formula. Sodium lauryl sulfate and sodium stearyl fumerate provided tablets below 5 kp in hardness at this 30% w/w level in the formula. Results are provided to show that this class of lubricants does not retard dissolution and alone or in combination with other lubricants can be used at any level where an acceptable lubrication and tablet hardness can be obtained. The sodium chloride tablets exhibited some sticking in the 7 to 13 Kp range of hardness, but this went away between 15 and 20 Kp hardness. Hardness for the tablets was not a problem with this excipient. At a 30% w/w level in the formula the following dissolution results for Potassium Oxaprozin was obtained: N=6 for all testing except where noted.

|  | 10 MIN | 15 MIN | 20 MIN | 30 MIN | 45 MIN | 60 MIN |
|---|---|---|---|---|---|---|
| Formula containing 30% w/w Sodium Chloride: | | | | | | |
| Concentration | 92.3 | 96.6 | 98.4* | 97.8 | 97.7 | 98.1 |
| Standard Deviation | 4.7 | 4.5 | 1.6* | 2.2 | 2.4 | 1.9 |
| Formula containing 30% w/w Sodium Lauryl Sulfate | | | | | | |
| Concentration | 64.0 | 81.0 | 91.8 | 100.3 | 100.5 | 100.4 |
| Standard Deviation | 2.9 | 3.0 | 3.4 | 3.9 | 4.3 | 4.2 |
| Formula containing 30% w/w Sodium Stearyl Fumerate | | | | | | |
| Concentration | 37.3 | 51.9 | 64.5 | 83.9 | 99.3 | 103.0 |
| Standard Deviation | 1.7 | 1.6 | 1.5 | 2.1 | 1.2 | 0.7 |

*Result is for average of 5 samples.

The conclusion that can be drawn for this class of soluble lubricants, when used in formulating Potassium Oxaprozin tablets, is that any level of these excipients that will give an acceptable tablet both in appearance and hardness will also provide acceptable bioavailability and can be used for use in this product. The limits on the use of the soluble lubricants is the constraints of the size of the tablet to be formed. If 30% levels of an excipient are achievable in the formula and the dissolution criteria is met, than it has been assumed that there is no upper limit for use of the particular lubricant or binder, and the formulations herein as much of the excipient as can be practicably used in making a tablet of realistic size can be used.

Water-soluble lubricants, and the percent ranges thereof of the total tablet weight, which may be employed in the formulations of the present invention include sodium lauryl sulfate (preferably from about 0% to about 20%, more preferably from about 0% to about 10%, most preferably from about 0% to about 5%) and sodium stearyl fumerate (preferably from about 0% to about 5%, more preferably from about 0.25% to about 2%, most preferably from about 0.5% to about 1%).

It is also possible to combine more than one of the lubricants described above in the ranges described therefor, for example magnesium stearate at about 0.25% with stearic acid at about 1%. Further, it is possible to combine one or more of the lubricants described above with small quantities of other lubricants, such as boric acid, sodium benzoate+ sodium acetate, sodium chloride, DL-leucine, Carbowax 4000, Carbowax 6000, sodium oleate, sodium benzoate, sodium acetate, sodium lauryl sulfate, magnesium lauryl sulfate, glycerol palmitate stearate, glycerol behenate, paraffin, PEG behenate, sodium stearyl lactylate, magnesium laurel sulfate, sodium stearate and ucuuba wax (virola surinamensis seeds).

Glidants

The optional glidant component of the pharmaceutical formulations of the present invention aids the flow of a granulation in a mechanical press so that it is sufficient to maintain uniform weight control from tablet to tablet. It also helps prevent the tablet or other compressible form of the formulation from adhering to the upper and lower punches of the press. If the level of glidant is too low, the weight variation from tablet to tablet may be too great, and the tablets may not be uniform. If, on the other hand, the level of glidant is too high, it will hinder the binding characteristics of the tablet, and the physical quality of the tablet may begin to decrease (the compressability of the formulation into tablets and/or the dissolution of any resulting tablets may be adversely affected). Thus, the formulations of the invention optionally contain a sufficient amount of glidant to ensure that the flow of a granulation containing the formulations in a mechanical press is sufficient to maintain uniform weight control from tablet to tablet, and to prevent the tablets from adhering to the upper and lower punches of the press, but an amount which is less than that which will hinder the binding characteristics of the tablet.

Any glidant may optionally be employed in the formulations of the present invention. Glidants, and the percent ranges thereof of the total tablet weight, which may be employed in the formulations of the present invention include talc (preferably from about 0% to about 10%), cornstarch USP (preferably from about 0% to about 10%), pregelatinized cornstarch (preferably from about 0% to about 10%) and silicon dioxide (preferably from about 0% to about 0.5%).

Anti-Adherents

The optional anti-adherent component of the pharmaceutical formulations of the present invention aids the flow of a granulation in a mechanical press so that it is sufficient to maintain uniform weight control from tablet to tablet. It also helps prevent the tablet or other compressible form of the formulation from adhering to the upper and lower punches of the press. If the level of anti-adherent is too low, the weight variation from tablet to tablet may be too great, and the tablets may not be uniform. If, on the other hand, the level of anti-adherent is too high, it will hinder the binding characteristics of the tablet, and the physical quality of the tablet may begin to decrease, (the compressability of the formulation into tablets and/or the dissolution of any resulting tablets may be adversely affected). Thus, the formulations of the invention optionally contain a sufficient amount of anti-adherent to ensure that the flow of a granulation containing the formulations in a mechanical press is sufficient to maintain uniform weight control from tablet to tablet, and to prevent the tablets from adhering to the upper and lower punches of the press, but an amount which is less than that which will hinder the binding characteristics of the tablet.

Any anti-adherent may optionally be employed in the formulations of the present invention. Anti-adherents, and the percent ranges thereof of the total tablet weight, which may be employed in the formulations of the present invention include talc (preferably from about 0% to about 10%), cornstarch USP (preferably from about 0% to about 10%), pregelatinized cornstarch (preferably from about 0% to about 10%), silicon dioxide (preferably from about 0% to about 0.5%), DL-leucine (preferably from about 0% to about 10%), sodium lauryl sulfate (preferably from about 0% to about 10%) and metallic stearates, such as magnesium, calcium and zinc stearates (less than 0.976%, preferably from about 0% to about 0.25%, most preferably 0%).

Fillers

The function of the optional filler component of the pharmaceutical formulations of the invention is to take up space. Thus, the percentage of filler employed is not critical, with the exception that the use of insoluble fillers in too large of a quantity in a tablet may retard the time the tablet takes to disintegrate and, thus, may adversely affect dissolution. A person of ordinary skill in the art will be able to determine this quantity with respect to a particular filler.

Insoluble fillers, and the percent ranges thereof of the total tablet weight, which may optionally be employed in the formulations of the present invention include starches, such as cornstarch, potato starch, tapioca starch and rice starch (from about 0% to about 99%, most preferably 0% to 30%), modified starches, such as sodium starch glycolate and pregelatinized cornstarch (from about 0% to about 99%, most preferably 0% to 30%) and microcrystalline cellulose (from about 0% to about 49.29%, preferably from about 0% to about 27%, most preferably from about 0% to about 12.7%).

Any soluble filler may optionally be employed in the formulations of the present invention. Soluble fillers, and the percent ranges thereof of the total tablet weight, which may be employed in the formulations of the present invention include lactose, sucrose, dextrose, mannitol and sorbitol, each from about 0% to about 65%, preferably from about 5% to about 50%, most preferably from about 8% to about 15%.

Disintegrants

The function of the optional disintegrant component of the pharmaceutical formulations of the invention is to aid the disintegration of tablets (the ability of the tablets to break into small pieces) compressed from these formulations. Disintegrants, and the percent ranges thereof of the total weight, which may optionally be employed in the formulations of the present invention include corn starch, NF purity 21, croscarmellose Na, microcrystalline cellulose PH-101, microcrystalline cellulose PH-102, polacrilin potassium IRP-88, sodium starch glycolate, each from about 0% to about 10%, preferably from about 1% to about 5%, most preferably from about 2% to about 3%.

(3) Utility

The potassium, sodium and Tris oxaprozin salt formulations of the present invention are useful as analgesic agents for the treatment of pain in animals, and as anti-inflammatory agents for the treatment of inflammation and inflammation-associated disorders, such as rheumatoid arthritis and osteoarthritis, and related disorders and conditions.

The novel pharmaceutical formulations of the present invention would be useful for the treatment of inflammation in an animal, and for treatment of other inflammation-associated disorders, such as an analgesic in the treatment of pain and headaches, or as an antipyretic for the treatment of fever. For example, the novel pharmaceutical formulations of the present invention would be useful to treat arthritis, including but not limited to rheumatoid arthritis, spondyloarthopathies, gouty arthritis, systemic lupus erythematosus, osteoarthritis and juvenile arthritis. Such pharmaceutical formulations would be useful in the treatment of gastrointestinal conditions such as inflammatory bowel syndrome, Crohn's disease, gastritis, irritable bowel syndrome and ulcerative colitis. Pharmaceutical formulations of the present invention would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like.

The pharmaceutical formulations of the present invention are useful as anti-inflammatory agents, such as for the treatment of arthritis, with the additional benefit of having significantly less harmful side effects and good gastrointestinal tolerance.

In the development of any orally-administered solid pharmaceutical formulation which contains an active ingredient for the treatment of pain, the preferred goal is to have the largest percentage of active ingredient dissolve and, thus, enter a patient's bloodstream, in the shortest period of time and, as a result, have an onset of action of the active ingredient in a relatively short period of time, such as one hour. The pharmaceutical formulations of the present invention generally have the characteristic that about 75% of the active ingredient (potassium, sodium or Tris salt of oxaprozin) becomes dissolved in phosphate buffer media within about 30 minutes, with some of these formulations having about 95% of the active ingredient dissolving in such media within about 30 minutes. The dissolution experiments which are described hereinbelow show that tablet pharmaceutical formulations of the invention containing only the active ingredient (potassium, sodium, or Tris salt of oxaprozin), have the characteristic that about 80% of the active ingredient becomes dissolved in phosphate buffer media within 15 minutes. The other dissolution experiments which are described hereinbelow show that tablet pharmaceutical formulations of the invention containing the potassium salt of oxaprozin and containing a percentage of magnesium stearate of the total tablet weight which is equal to, or greater than, 0.976% do not have the above-described characteristic. These experiments also show that the preferred pharmaceutical formulation of the present invention which contains no magnesium stearate generally has about 90% of the active ingredient dissolved in phosphate buffer media within about 15 minutes, with about 100% of the active ingredient dissolved within about 30 minutes.

(4) Methods of Preparation

In general, the pharmaceutical compositions of the present invention may be prepared by the methods illustrated in the general reaction schemes presented below, or by modifications thereof, using readily-available starting materials, reagents and conventional synthesis procedures.

Oxaprozin contains an acidic functional group and, thus, is capable of forming pharmaceutically-acceptable potassium, sodium and Tris salts with pharmaceutically-acceptable bases. The term "pharmaceutically-acceptable salts" in these instances refers to the relatively non-toxic, inorganic and organic base additional potassium, sodium and Tris salts of oxaprozin. These salts can be prepared in the process of the final isolation and purification of the oxaprozin, or by separately reacting the purified oxaprozin in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, S. M. Berge et al., "Pharmaceutical Salts," *J. Pharm. Sci.*, 66:1–19 (1977), which is incorporated herein by reference.

Methods for preparing pharmaceutical formulations of the present invention include the step of bringing into association the active ingredient (the potassium, sodium or Tris salt of oxaprozin) with a suitable lubricant, or with a suitable lubricant and a suitable binder, and, optionally, with one or more accessory ingredients. In general, the formulations are prepared by uniformly and intimately bringing into association the active ingredient with other ingredients of the formulations and, optionally, with one or more other ingredients, with liquid carriers, or finely divided solid carriers, and then shaping the product, for example, with a mechanical press, into pills, tablets, caplets or other compressed forms of the formulations.

General Reaction Scheme No. 1 shows the synthesis of the various salts of oxaprozin described herein (the sodium, potassium and Tris salts of oxaprozin). Oxaprozin in its acid form is commercially available, for example, from Katwijk Chemi BV, Steenbakkerstraat, NV.

To a stainless steel or glass-lined vessel is charged oxaprozin, followed by isopropanol (isopropyl alcohol). The mixture is heated to about 70° C., and the appropriate solution of aqueous base (e.g. potassium hydroxide, sodium hydroxide or Tris hydroxide) is added to the mixture until the desired pH end point (pH of about 9–13) is attained. To achieve complete conversion of the acid to the salt, a minimum of one stoichiometric equivalent of caustic agent must be added per equivalent of oxaprozin. Caustic shortage results in non-conversion of a portion of the oxaprozin acid. In such an instance, the resulting product will be a mixture of oxaprozin acid and oxaprozin salt.

The resulting solution is filtered in a manner known by those of skill in the art to insure particulate-free product. A portion of the solvent volume is removed by distillation at atmospheric pressure in a manner known by those of skill in the art. (The distillate is an azeotrope of isopropanol and water. Water remaining in the reaction mixture results in yield loss due to the solubility of the oxaprozin salt in water. Distillation volume is based on economic analysis, which balances distillation costs against yield.) Upon completion of the distillation, fresh isopropanol is added to the reaction mixture at reflux temperature. The solution is cooled to cause the product to crystallize. The product is isolated by centrifugation in a manner known by those of skill in the art, washed with isopropanol, and dried in a fluid bed or vacuum drier in a manner known by those of skill in the art to a product temperature not exceeding 120° C.

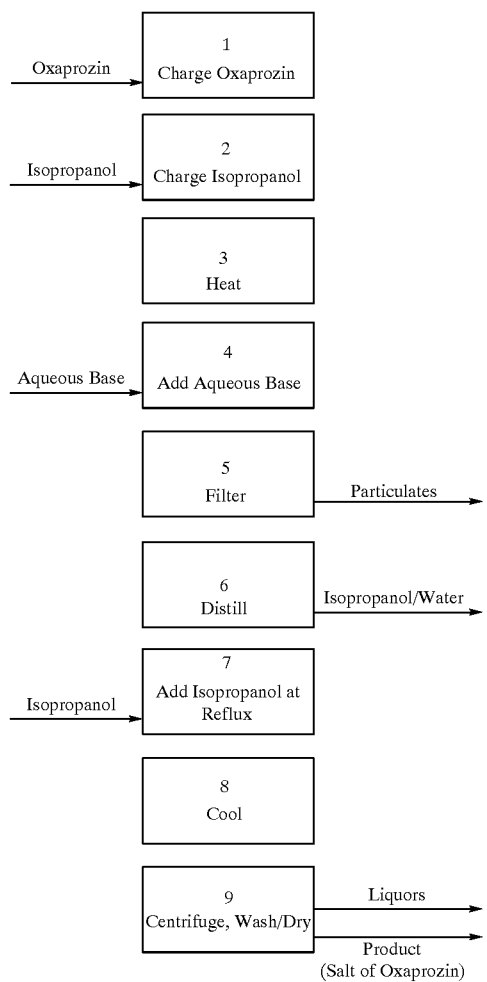

GENERAL REACTION SCHEME NO. 1

General Reaction Scheme No. 2 shows the production of the compressed pharmaceutical formulations of the present invention.

Granulation (converting the raw material, which is in powder form, to a compressable granulation) may be carried out in any mixer capable of high speed/high shear equipped with a spray wand and chopper. The dry potassium oxaprozin, sodium oxaprozin or Tris oxaprozin is placed into the mixer and mixed with the main impeller and the chopper on low speed for a period of time which is sufficient to break up any lumps that may be present in the raw material. For those pharmaceutical formulations of the present invention which contain binder, a suspension of a binder, such as pregelatinized corn starch, is prepared in a propeller-type mixer with a sufficient amount of purified water to make a sprayable solution of the suspension. The binder should be added slowly in order to avoid lumps in the suspension. It is preferable to include an additional 5% or so of binder in the mixture, which will remain in the mixer at the end of this process, in a manner known by those of skill in the art. The binder suspension is heated in a suitable heating unit, such as a jacketed steam kettle, and held at about 53° C. The mixer and chopper are turned on at low speed and the binder suspension is sprayed onto the raw material utilizing an airless spray system in a manner known by those of skill in the art. Once all of the liquid is applied, the mixer is allowed to run until a granulation is formed. If, at the end of the granulation step, the product appears to be lumpy, the entire granulation may be wet screened with an oscillating granulator or a mill, in a manner known by those of skill in the art, before the drying step.

Drying of the granulation may be carried out in any suitably sized fluid bed drier in a manner known by those of skill in the art. The wet granulation is placed into the product container and the bed is fluidized. The air temperature for drying is about 75° C. The granulation is dried to a moisture content of less than 2% w/w (there is less than 2 gm of water for every 100 gm of finished granulation product). Once the moisture content is correct, the granulation is sized through a #12 or other suitable screen in a manner known by those of skill in the art. Any milling equipment capable of being fitted with a #12 screen would be suitable.

Dry blending may be carried out in any V blender in a manner known by those of skill in the art. The dried, sized, granulation is loaded into the blender, and appropriate quantities of all optional ingredients, such as glidants and anti-adherents, are added to this mixture. The mixer is turned on and mixed for about 10 minutes. For those pharmaceutical formulations of the present invention which contain lubricant, the lubricant, such as stearic acid, is screened through a 30 mesh or other suitable screen in a manner known by those of skill in the art and added to the blender. A final mix time of about 7 minutes is used, then the mixture is withdrawn from the blender.

Compression of the resulting formulation into tablets, caplets or other compressible oral forms can be carried out on any suitable tablet press in a manner known by those of skill in the art, such as a rotary tablet machine capable of holding 0.3261"×0.7480" tooling. The granulation is loaded into the tablet machine hopper, and the machine is started to produce tablets, caplets or other compressible oral forms which have the desired physical specifications for the finished product. These specifications include acceptable disintegration, dissolution, hardness, size, weight variation and friability.

An optional coating of the resulting tablets, caplets or other compressible forms of the formulations with a film coating such as Opadry®, which may be obtained from Colorcon, Inc. (West Point, Pa.), may be accomplished in a manner known by those of skill in the art in any side-vented, perforated pan equipped with an air spray system. Such a coating makes the tablets easier to swallow, and enhances their pharmaceutical elegance. The tablets are loaded into the machine and the heat is turned on to warm the tablet bed. The coating process is carried out at a temperature that is preferably at least 50° C. An aqueous coating solution is prepared and applied to the tablets at a pan speed of approximately 7 RPM (rotations per minute). When the appearance of the tablets is acceptable (meets the desired pharmaceutical elegance), and an appropriate amount of solution is applied, the coating process is complete.

GENERAL REACTION SCHEME NO. 2

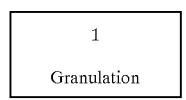

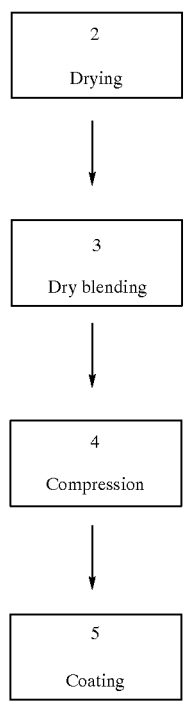

The conditions for carrying out the individual steps in each of the general reaction schemes presented above are conventional, well-known, and capable of wide variation. Other methods known in the art can also be used to synthesize the potassium, sodium and Tris salts of oxaprozin.

Because the salts of oxaprozin are photosensitive materials, they can be degraded by exposure to excessive light. Thus the chemical should not be exposed to excessive light during the process of manufacturing the pharmaceutical preparations of the present invention.

Besides inert diluents, the oral compositions can also include adjuvants such as wetting agents, emulsifying and suspending agents, sweetening, flavoring, coloring, perfuming and preservative agents.

(5) Dosage and Mode of Administration

The pharmaceutical compositions of the present invention are useful in treating pain, inflammation and/or inflammation-associated disorders in animals. A physician or veterinarian of ordinary skill in the art can readily determine whether or not a particular patient is in pain, or has inflammation or an inflammation-associated disorder.

The pharmaceutical compositions of the present invention, which will typically comprise a potassium, sodium or Tris salt of oxaprozin as an active ingredient by itself, in admixture with a pharmaceutically-acceptable lubricant, or in admixture with a pharmaceutically-acceptable lubricant and a pharmaceutically acceptable binder, and, optionally, with one or more other compounds, drugs, excipients or other therapeutic or non-therapeutic materials, are employed therapeutically and, thus, would generally be used under the guidance of a physician. Each ingredient of the pharmaceutical formulations of the present invention must be "acceptable" in the sense of being compatible with the other ingredients of the formulations and not injurious to the patient.

The appropriate dosage and form of administration of the pharmaceutical compositions of the present invention will be suitably selected by methods which are consistent with conventional pharmaceutical practices.

The pharmaceutical compositions of the present invention may be specially formulated for oral administration in a solid, compressible form and are formulated into pharmaceutically-acceptable dosage forms by conventional methods known to those of skill in the art.

Actual dosage levels of the active ingredients in the pharmaceutical compositions of this invention (potassium, sodium or Tris salt of oxaprozin) may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular oxaprozin salt employed, the route of administration, the time of administration, the rate of excretion of the particular oxaprozin salt being employed, the severity of the pain, inflammation or inflammation-associated disorder, the duration of the treatment, other ingredients, drugs, compounds, excipients and/or materials used in combination with the particular oxaprozin salt employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain, inflammation or inflammation-associated disorder. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a pharmaceutical formulation of the present invention will be that amount of the pharmaceutical formulation which is the lowest dose effective to produce a therapeutic effect. Such an effective dose will generally depend upon the factors described above. Generally, dosage levels in the range of from about 0.001 mg to about 10 g, more preferably from about 1 mg to about 3000 mg, still more preferably from about 1000 mg to about 2000 mg, and most preferably from about 1200 mg to about 1800 mg of pharmaceutical formulation per day are administered to a mammalian patient. However, the total daily usage of the pharmaceutical compositions of the present invention will be determined by an attending physician or veterinarian within the scope of sound medical judgement.

If desired, the effective daily dose of the active compound (potassium, sodium or Tris salt of oxaprozin) may be administered as two, three, four, five, six or more sub-doses administered separately at appropriate intervals throughout the day, optionally, in unit dosage forms. Formulations of the present invention are those which are suitable for oral administration. The formulations may conveniently be presented in unit dosage form. The amount of active ingredient (potassium, sodium or Tris salt of oxaprozin) which can be combined with a carrier or other material to produce a single dosage form will vary depending upon the host being treated, the particular mode of administration and all of the other factors described above. The amount of active ingredient which can be combined with a carrier or other material to produce a single dosage form will generally be that amount of the compound which is the lowest dose effective to produce a therapeutic effect. Generally, out of one hundred percent, this amount will range from about 1 percent to about 100 percent of active ingredient, preferably from about 50 percent to about 95 percent, most preferably from about 70 percent to about 90 percent, preferably about 83%.

While the various aspects of the present invention are described herein with some particularity, those of skill in the art will recognize numerous modifications and variations which remain within the spirit of the invention. These modifications and variations are within the scope of the invention as described and claimed herein.

(6) Examples

The following examples describe and illustrate the methods for the preparation of the formulations of the present invention, as well as other aspects of the present invention, including the unsuccessful experiments described hereinabove, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the pharmaceutical formulations of the present invention.

In the examples, all parts are by weight unless otherwise indicated.

All equipment employed in the examples is commercially available.

Unless otherwise indicated in a particular example, all starting materials employed in the examples are commercially available. Sources for these starting materials and pieces of equipment employed in the examples include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), Chemical Dynamics Corp. (South Plainfield, N.J.), Pfaltz & Bauer (Waterbury, Conn.), G.D. Searle & Co. (Augusta, Ga.), Degussa (Ridgefield, N.J.), Witco Corp. (Greenwich, Conn.), Colorcon (West Point, Pa.), FMC Corp. (Philadelphia, Pa.), Speciality Minerals Inc. (Easton, Pa.), National Starch (Bridgewater, N.J.), Cabot Corp. (Tuscola, Ill.), W. R. Grace (Baltimore, Md.), Tanabe USA (San Diego, Calif.), Henkel Corp. (LaGrange, Ill.), Mallinckrodt (St. Louis, Mo.), Karlshamns (Karshamn, Sweden), US Borax (Valencia, Calif.), Niacet Corp. (Niagara Falls, N.Y.), Cargill Inc. (Eddyville, Iowa), Morton Salt (Chicago, Ill.), Union Carbide (Danbury, Conn.), Strahl & Pritsch (West Babylon, N.Y.), DGF Stoess (Sioux City, Iowa), Chart Corp. (Paterson, N.J.), ISP Corp. (Wayne, N.J.), Aqualon (Wilmington, Del.), Mendell (Paterson, N.Y.), Quest International (Norwich, N.Y.), Archer Daniel Midland (Decatur, Ill.), Roquette (Keokuk, Ill.), Wyckoff Chemical Company, Inc. (South Haven, Mich.), Solchem Italiana spa (Milan, Italy), Katwijk Chemie BV (Steenbakkerstraat, The Netherlands), Irotec Laboratories (Little Island, Cork, Ireland), Sumita Fine Chemicals Co., Ltd. (Osaka, Japan), Niro Inc., Aeromatic-Fielder Division (Columbia, Md.), Lee Industries, Inc. (Philipsburg, Pa.), Paul A. Mueller Inc. (Springfield, Mo.), DCI, Inc. (St. Paul, Minn.), Quadro, Inc. (Millburn, N.J.), Fitzpatrick & Co. (Elmhurst, Ill.), Glatt Air Techniques (Ramsey, N.J.), Patterson-Kelly (Stroudsberg, Pa.), Gemco Inc. (Middlesex, N.J.), Manesty Tablet Presses—Thomas Engineering (Hoffman Estates, Ill.), Cadmac Tablet Presses—Key International Inc. (Englichtown, N.J.), Stokes Tablet Presses (Philadelphia, Pa.), Thomas Engineering (Hoffman Estates, Ill.), Natoli Engineering Co. (Chesterfield, Mo.), Vector Corp. (Marion, Iowa), O'Hara Manufacturing (Toronto, Ontario, Canada), Graco Inc. (Minneapolis, Minn.), Watson-Marlow (Wilmington, Mass.) and Spraying Systems Co. (Wheaton, Ill.). The synthesis procedures for any starting materials employed in the examples which are not commercially available are described in the examples.

All patents and publications referred to in the examples, and throughout the specification, are hereby incorporated herein by reference, without admission that such is prior art.

EXAMPLE 1

Initial Unsuccessful Experiments Conducted when Attempting to make a Formulation for the Potassium Salt of Oxaprozin (1) First Experiment In this experiment, the potassium salt of oxaprozin was directly substituted for the acid form of oxaprozin in DAYPRO®, with the resulting formulation:

| Potassium Salt of Oxaprozin 678 mg Tablet Formulation | | |
|---|---|---|
| Ingredients | Mg/Tablet | % Composition |
| Oxaprozin Potassium Salt | 677.9 mg | 68.3% |
| Microcrystalline Cellulose PH-101, NF | 80.7 mg | 8.1% |
| Corn Starch, NF | 19.8 mg | 2.0% |
| Methylcellulose A15LVP, USP | 29.7 mg | 3.0% |
| Water, mg/Tab | 291.2 mg | |
| Polacrilin Potassium IRP-88, NF | 29.7 mg | 3.0% |
| Microcrystalline Cellulose PH-102, NF | 142.4 mg | 14.4% |
| Magnesium Stearate, NF | 11.8 mg | 1.2% |
| Total | 992.0 mg | 100.0% |

A 12 kg batch of granulation was prepared in a Niro Fielder PMA 1200 high speed/high shear granulator (Niro, Inc., Aeromatic—Fielder Division, Columbia, Md.) in the manner described below.

The potassium oxaprozin, microcrystalline cellulose PH 101, and corn starch were loaded into the machine and a solution of water and methylcellulose was sprayed into the mass. Once a granulation had formed, the granulated mass was dried in a fluid bed drier (Niro Fielder Aeromatic Division, Columbia, Mass.). Once the dry mass was sized through a screen, it was combined with the remaining ingredients. The mixing was done in a Crossflo V blender (Patterson-Kelly, Stroudsberg, Pa.). A tabletting trial was attempted on a rotary tablet press (Kilian & Co., Horsham, Pa.). The granulation did not tablet well due to severe sticking of the granulation to the punch faces. The level of magnesium stearate was increased from 1.2% to 2.0% w/w and the sticking problem was corrected. Disintegration experiments were performed in accordance with the United States Pharmacopia (USP), with tablets containing the above formulation, in 900 ml of water (purified by reverse osmosis) as the medium with apparatus without a disc at 37° C. In each disintegration experiment, six tablets were tested per basket. By visual observation, when the last tablet had completely disappeared, a given time interval was obtained. The tablets in the above formulation had disintegration times in excess of 45 minutes.

The remaining granulation was taken out of the tablet machine and split into two equal parts. The first part had a disintegration aid, croscarmellose sodium, added at 3% w/w the second part used another disintegration aid, sodium starch gycolate at 3% w/w. This was again carried out in the above-described V blender. The two formulations were compressed on the above-described rotary tablet press.

Dissolution experiments were performed in accordance with the USP, with tablets containing the above formulations, as well as with Daypro®, in 1000 ml of pH 7.4 phosphate buffer as the medium with Apparatus 2 (paddle) at 75 rotations per minute (rpm) at 37° C. In each dissolution experiment, six tablets were tested in six different vessels. A percentage of the tablets dissolved at a given time interval was obtained, and the means and standard deviation were calculated in a manner known by those of skill in the art. As is shown in the table presented below, the tablets compressed from the two above-described formulations showed poor dissolution results when compared with Daypro®.

| | Dissolution results for initial potassium salt formulations | | | |
|---|---|---|---|---|
| | Percent Dissolved | | | |
| Time Minutes | Potassium Oxaprozin Salt (1.2% Magnesium Stearate) | Potassium Oxaprozin Salt (2% Magnesium Stearate and 3% Croscarmellose Sodium) | Potassium Oxaprozin Salt (2% Magnesium Stearate and 3% Sodium Starch Glycolate) | Daypro ® |
| 0 | 0 | 0 | 0 | 0 |
| 15 | 14.6 | 13.6 | 13.8 | 79.8 |
| 30 | 22.5 | 22.9 | 21.6 | 93.6 |
| 45 | 35.4 | 38.5 | 32.6 | 96.8 |
| 60 | 54.9 | 49.1 | 59.8 | 98.4 |
| 75 | 74.6 | 76.4 | 50.9 | 98.4 |
| 90 | 96.2 | 90.5 | 67.5 | 98.4 |

(2) Second Experiment

In this experiment, the disintegrant croscarmellose sodium was added, and the binder was changed to hydroxypropyl cellulose, with the resulting formulation:

| Potassium Salt of Oxaprozin 678 mg Tablet Formulation | | |
|---|---|---|
| Ingredients | Mg/Tablet | % Composition |
| Oxaprozin Potassium Salt | 677.9 mg | 67.8% |
| Microcrystalline Cellulose PH-101, NF | 95.0 mg | 9.5% |
| Croscarmellose Na, AcDiSol | 22.0 mg | 2.2% |

-continued

Potassium Salt of Oxaprozin 678 mg Tablet Formulation

| Ingredients | Mg/Tablet | % Composition |
|---|---|---|
| Polyoxyl 40 Stearate Myrj-52S | 4.0 mg | 0.4% |
| Hydroxypropyl Cellulose, Klucel EF | 20.0 mg | 2.0% |
| Water | 111.5 mg | |
| Ethanol | 89.4 mg | |
| Croscarmellose Na, AcDiSol | 22.0 mg | 2.2% |
| Microcrystalline Cellulose PH-101, NF | 143.1 mg | 14.3% |
| Magnesium Stearate, NF | 16.0 mg | 1.6% |
| Total | 1000.0 mg | 100.0% |

The oxaprozin potassium, microcrystalline cellulose PH 101, and the croscarmellose sodium, were placed into a Fuji granulator (Fuji Sangyo Co LTD, Osaka, Tokyo, Japan.) The impeller was turned on to mix the ingredients. A granulation solution of the hydroxypropyl cellulose, polyoxyl 40 stearate, water and ethanol was prepared in a separate stainless steel container with constant mixing. The resulting solution was sprayed on the dry mass over 12 minutes with the impeller and chopper on. The resulting granulation was dried in a forced hot air oven (Blue M, Blue Island, Ill.). The resulting granulation was sized through a 14 mesh screen. The sized granulation, croscarmellose sodium, microcrystalline cellulose PH 101, and magnesium stearate were mixed in a V blender. The granulation was removed from the blender and compressed on a rotary tablet machine. The tablets were compressed without sticking to the punch faces.

Disintegration experiments were performed on the tablets in the manner described hereinabove. Disintegration times for the tablets were greater than 1 hour.

It was decided to add more microcrystalline cellulose in an attempt to improve the disintegration of the tablets. The existing granulation was mixed with 50% w/w of microcrystalline cellulose in a V blender. The tablet weight was increased from 1000 mg to 1500 mg. Another tabletting attempt was made, but the desired tablet weight could not be attained on the machine. The tablets were compressed at 1300 mg. The disintegration times for this second formulation of tablets were approximately 45 minutes.

(3) Third Experiment

In this experiment, the disintegrant crospovidone was added, with the resulting formulation:

Potassium Salt of Oxaprozin 678 mg Tablet Formulation

| Ingredients | Mg/Tablet | % Composition |
|---|---|---|
| Oxaprozin Potassium Salt | 677.9 mg | 83.5% |
| Corn Starch, NF | 80.1 mg | 9.9% |
| Crospovidone, Polyplasdone XL-10 | 42.0 mg | 5.2% |
| Water | 147.4 mg | |
| Magnesium Stearate, NF | 11.8 mg | 1.5% |
| Total | 811.8 mg | 100.0% |

The potassium oxaprozin, corn starch, and crospovidone were mixed in the Fuji granulator. Water was sprayed on the mixing mass to form a granulation over 12 minutes. Granulation was dried in an oven. The dried granulation was sized through a 14 mesh screen. The resulting sized granulation was combined in a V blender with magnesium stearate. The blend was withdrawn and transferred to a rotary tablet press. The attempt at tabletting was unsuccessful due to severe sticking to the punch faces of the tablet press. In addition, the tablets capped (broke apart upon ejection from the mechanical press.)

In an attempt to salvage this experiment, it was determined that microcrystalline cellulose and additional crospovidone and magnesium stearate would be added to the formulation as follows:

| | mg/tablet | % Composition |
|---|---|---|
| Base granulation from the formulation described directly above | 811.8 mg | 67.6% |
| Microcrystalline Cellulose | 338.0 mg | 28.2% |
| Crospovidone | 42.0 mg | 3.5% |
| Magnesium Stearate | 8.2 mg | 0.7% |
| | 1200.0 mg | 100.0% |

The granulation, microcrystalline cellulose, crospovidone and magnesium stearate were mixed in a V blender. The blend was withdrawn from the blender and a tabletting trial was attempted. The tablets did not stick or cap, but the tablet weight of 1200 mg could not be attained. The tablets were compressed at a maximum weight of 1100 mg.

Disintegration experiments were performed on the tablets in the manner described hereinabove. The disintegration times for the tablets were 45 minutes to 1 hour.

(4) Fourth Experiment

In this experiment, the disintegrant crospovidone and the lubricant sodium laurel sulfate were added, and the binder was changed to povidone K-90, with the resulting formulation:

Potassium Salt of Oxaprozin 678 mg Tablet Formulation

| Ingredients | Mg/Tablet | % Composition |
|---|---|---|
| Oxaprozin Potassium Salt | 677.9 mg | 94.4% |
| Sodium Lauryl Sulfate | 10.1 mg | 1.4% |
| Crospovidone, Polyplasdone XL-10 | 17.0 mg | 2.4% |
| Ethanol | | |
| PVP, Povidone K-90 | 13.0 mg | 1.8% |
| Total | 718.0 mg | 100.0% |

The potassium oxaprozin, sodium laurel sulfate, and crospovidone were mixed in the Fuji granulator. A granulating solution of polyvinylpyrrolidone and water was prepared in a separte container with mixing. The granulation solution was applied to the mixing mass by slow spraying. This process did not form a granule. A doughy mass formed and the trial was terminated with no further action.

(5) Fifth Experiment

In this experiment, the disintegrant starch and the glidant talc were added, and the binder was changed to povidone K-90, with the resulting formulation presented hereinbelow.

| Potassium Salt of Oxaprozin 678 mg Tablet Formulation | | |
|---|---|---|
| Ingredients | Mg/Tablet | % Composition |
| Oxaprozin Potassium Salt | 677.9 mg | 95.2% |
| Crospovidone, Polyplasdone XL | 21.4 mg | 3.0% |
| Water | 188.5 mg | |
| PVP, Povidone K-90 | 13.0 mg | 1.8% |
| Total | 712.3 mg | 100.0% |

The potassium oxaprozin and crospovidone were mixed in a Fuji granulator. A granulating solution of polyvinylpyrrolidone and water was prepared in a separate container. The granulation was dried in an oven and then sized through a 14 mesh screen. This finished granulation was utilized in the following formulation.

| Ingredients | Mg/Tablet | % Composition |
|---|---|---|
| Base Granulation | 712.3 mg | 71.2% |
| Crospovidone, Polyplasdone XL | 88.2 mg | 8.8% |
| Microcrystalline Cellulose PH-102, NF | 70.0 mg | 7.0% |
| Pregelatinized Starch, Starch 1500 | 100.0 mg | 10.0% |
| Talc | 20.0 mg | 2.0% |
| Magnesium Stearate | 10.0 mg | 1.0% |
| Total | 1000.0 mg | 100.0% |

The granulation, crospovidone, microcrystalline cellulose PH 102, pregelatinized corn starch, talc, and magnesium stearate were blended in a V blender. The resulting blend was transferred to a rotary tablet machine. The tabletting attempt was successful and the tablets did not stick to the punches or cap in the machine.

Disintegration experiments were performed on the tablets in the manner described hereinabove. The disintegration times for the tablets was 29 to 35 minutes.

(6) Sixth Experiment

In this experiment, lactose anhydrous DTG was added, with the resulting formulation:

| Potassium Salt of Oxaprozin Formulation | | |
|---|---|---|
| Ingredients | Mg/Tablet | % Composition |
| Base Granulation | 712.3 mg | 71.2% |
| Crospovidone, Polyplasdone XL | 88.2 mg | 8.8% |
| Lactose Anhydrous DTG | 70.0 mg | 7.0% |
| Pregelatinized Starch, Starch 1500 | 100.0 mg | 10.0% |
| Talc | 20.0 mg | 2.0% |
| Magnesium Stearate | 10.0 mg | 1.0% |
| Total | 1000.0 mg | 100.0% |

The granulation, crospovidone, lactose anhydrous DTG, pregelatinized corn starch, talc, and magnesium stearate were mixed in a V blender. The blend was transferred to a rotary tablet machine. A tabletting trial was attempted. The tabletting was successful and the tablets did not stick to the punch faces or cap in the machine. Disintegration experiments were performed on the tablets in the manner described hereinabove. The disintegration times for this formulation were greater than 1 hour.

(7) Seventh Experiment

In this experiment, which was the first successful experiment, the lubricant magnesium stearate was removed and corn starch was employed as the binder, with the resulting formulation:

| Potassium Salt of Oxaprozin 677.9 mg Tablet Formulation | | |
|---|---|---|
| Ingredients | Mg/Tablet | % Composition |
| Oxaprozin Potassium Salt | 677.9 mg | 95.3% |
| Corn Starch, USP | 15.4 mg | 2.2% |
| Water | 173.4 mg | |
| Silicon Dioxide, Aerosil 200 | 3.5 mg | 0.5% |
| Stearic Acid | 14.2 mg | 2.0% |
| Total | 711.0 mg | 100.0% |

The potassium oxaprozin was put into the Fuji granulator. In a separate container, a starch paste was prepared using water. The starch paste was applied to the mixing mass by spraying over 12 minutes. The resulting granulation was dried and sized through a 12 mesh screen. The sized granulation was mixed with the silicon dioxide and the stearic acid in a V blender. The blend was transferred to a rotary tablet machine for a tabletting trial, which was successful.

Disintegration experiments were performed on the tablets in the manner described hereinabove. The disintegration times for this formulation were 8 to 10 minutes. This formulation was also tested for dissolution in the manner described hereinabove and the results are presented below.

| Dissolution Results for First Successful Potassium Oxaprozin Formulation | |
|---|---|
| Time Minutes | Potassium Salt of Oxaprozin Formulation |
| 0 | 0.0 |
| 10 | 82.6 |
| 15 | Not Tested |
| 20 | 101.0 |
| 30 | 101.1 |
| 45 | 101.1 |
| 60 | 101.1 |

EXAMPLE 2

Oxaprozin Potassium Salt 600 Mg Tablets 600 mg film-coated oxaprozin potassium salt tablets were manufactured in the manner described below.

To a 2000 gallon stainless steel vessel with fixed baffles (available from Alloy Fab, South Plainfield, N.J.), equipped multi-speed agitator drive unit (available from Pfaudler, Rochester, N.Y.), was charged 688 kg (2.35 k-mole) of oxaprozin (G.D. Searle & Co., Augusta, Ga.) followed by 3689 kg isopropanol. The resulting mixture was heated to 70° C. (using 180° C. steam piped through the reactor's half-piped coils) at a rate of 1.5–2° C. (controlled by a Fisher Provox controller, available from Fisher Controls, Marshalltown, Iowa). Approximately 292 kg of 45% liquid potassium hydroxide (2.35 k-mole; 1 molar equivalent relative to oxaprozin) was added to the mixture until a final pH of 10–14 was reached. pH measurement (meter available from Bailey TBI, Carson City, Nev.) is used to confirm that proper stoichiometry has been achieved. The above solution was filtered (through a multiple-plate Niagra filter, available from AMETEK, Paoli, Pa., and fitted with 5–10 micron porosity paper, available from Customs Paper Group, Rochester, Mich.) to another 2000 gallon stainless vessel (as previously described), followed with a rinse of 275 kg of isopropanol to insure yield preservation. The resulting batch was heated (again using 180° C. steam piped through the reactor's coils) to reflux temperature and approximately 1750 liter of isopropanol/water azeotrope was removed by distillation to an ending temperature of approximately 83° C. (The azeotrope was condensed in a primary condenser using water at approximately 7° C. and a secondary condenser using methanol/water "brine" at −35° C.) After completion of distillation, 1106 kg of isopropanol was added to the product mixture while maintaining reflux temperature at approximately 83° C.

The above mixture was cooled to 5° C. The resulting crystallized product was isolated by centrifugation (using either a Tolhurst or Delaval 48" basket centrifuge, available from AMETEK, Paoli, Pa., with the basket spinning at 700–800 rpm fitted with cloth having an average porosity of 5–10 microns, available from KETEMA, El Cajon, Calif.), washed with approximately 50 kg of isopropanol per centrifuge load, and dried (at −60 kPa and 60° C. using a rotary vacuum tumble dryer, available from Patterson-Kelley, East Stroudsburg, Pa., or using a Fitzair fluid bed dryer, available from Fitzpatrick, Elmhurst, Ill., with the inlet temperature set at 212° C. and the cutoff temperature set a 225° C.) Approximately 700 kg of the oxaprozin potassium salt were obtained by the procedure.

305.9 kg of the potassium salt of oxaprozin was placed into a Niro Fielder PMA 1200 high speed/high shear granulator (Niro, Inc., supra.), and mixed for 3 minutes at 70 RPM with the chopper at slow speed. While this mixing was occurring, a suspension of 8.4 kg of pregelatinized corn starch, NF and 68.8 kg of purified water was combined in a stainless steel jacketed mixing tank (Lee Industries, Inc., Philipsburg, Pa.), mixed at a blade speed of 100% for ten minutes and then warmed to 53° C. with the homogenizer at 60%. (The pregelatinized corn starch was added slowly in order to avoid lumps in the suspension.) The warm suspension was sprayed into the mixing potassium salt of oxaprozin with a Graco model #954–383 pump equipped with a #95/10 nozzle sprayer (Graco Inc., Minneapolis, Minn.). The resulting mixture was wet milled through a Quadro Comil Model 198 S wet mill equipped with a 1" screen. The mixture was dried in a fluid bed drier (Quadro, Inc., supra.) with a system air flow of 5000 CFM (cubic feet per minute), a 37% inlet air opening, and an air intake temperature of 75° C. The moisture content was approximately 2% (and should be no greater than this). 1.8 kg of colloidal silicon dioxide, NF was added to this mixture, and the resulting mixture was milled through a fluid air mill model 007 equipped with a 0.094 screen at 50% screw feed and 60% rotor speed (Quadro, Inc., Millburn, N.J.). The mixture was transferred to a crossflo V blender (Patterson-Kelly, supra.) and preblended for 10 minutes. 47.1 kg of microcrystalline cellulose, NF was added to the mixture, and the mixture was blended for 10 minutes. 7.2 kg of stearic acid, NF was added to the mixture, and the mixture was blended for 7 minutes.

The resulting material was compressed into core tablets using a Manesty Model MK4 tablet press (Manesty Tablet Presses, Thomas Engineering, Hoffman Estates, Ill.), in a manner known by those of skill in the art. The resulting core tablets were white, capsule shaped and 0.3261"×0.7480" in size.

The core tablets were film coated with an aqueous solution of Opadry® (Colorcon, West Point, Pa.) at a rate of 400 ml per minute using a Thomas Engineering Accela Cota model 60 DXL film coater (Thomas Engineering, Hoffman Estates, Ill.), in a manner known by those of skill in the art. The film coater was set at an air volume of 2600 CFM, a pan speed of 4.0 rotations per minute and an intake temperature of 50° C., with jogging of the film coater for 3 seconds every 30 seconds. The exhaust temperature, which should never fall below 35° C., was maintained at 35° C., and the inlet temperature, which should never fall below 43° C., was maintained at 43°C. The resulting tablets were blue in color.

Because the potassium salt of oxaprozin is a photosensitive material, this chemical was protected against excessive exposure to light during the entire manufacturing process described above.

The process described above resulted in the manufacture of 350,000 tablets having the following components, and quantities thereof:

| Component | Quantity (Mg per Tablet) | Percent of the Composition |
|---|---|---|
| Potassium Salt of Oxaprozin | 677.9 mg | 82.67% |
| Pregelatinized Corn Starch, NF | 17.7 mg | 2.16% |
| Water, USP | 159.3 mg | 0% |
| Colloidal Silicon Dioxide, NF | 4.0 mg | 0.49% |
| Microcrystalline Cellulose, NF | 104.4 mg | 12.73% |
| Stearic Acid, NF | 16.0 mg | 1.95% |
| Total | 820.0 mg | 100.00% |

The dissolution data for this formulation are described with other dissolution data hereinbelow in Example 5. The dissolution experiments were performed in the manner described in Example 1.

EXAMPLE 3

Oxaprozin Sodium Salt

To a 3 liter, 3-neck round bottom (3NRB) flask, fitted with agitator (all equipment available from standard laboratory supply houses such as Fisher or Scientific Products), was charged 293.1 g (1 mole) of oxaprozin (Searle Chemical, August, Ga.), and followed by 2.05 liter isopropanol. The resulting mixture was heated to 70° C. (using electric heating mantle) and then was added approximately 495 ml of 2 N sodium hydroxide solution, prepared by dissolving 80.0 g of sodium hydroxide (ACS Reagent Grade obtained from Aldrich Chemical Co.) in and diluted to 1 liter volume with a solution of 15% water/85% methanol. (Normality of the sodium hydroxide solution was confirmed titrimetrically.)

The above mixture was allowed to cool to 40° C. over a period of one hour. The mixture was cooled to 3° C. using an ice bath, vacuum filtered on a Buchner funnel fitted with Whatman #4 paper, washed twice with 100 ml of isopropanol, then dried at 65° C. in a laboratory forced air dryer. This procedure produced 311.5 g of oxaprozin sodium salt.

Analysis Calculated for $C_{18}H_{14}NaNO_3 \cdot 1H_2O$: C, 64.88; H, 4.84; N, 4.20; 0, 15.22; Na, 7.29 (by residue on ignition) Found: C, 64.97; H, 4.98; N, 4.18; Na, 6.88 (by residue on ignition)

EXAMPLE 4

Oxaprozin Tris Salt

To a 3 liter 3NRB flask fitted with agitator (all equipment available from standard laboratory supply houses such as Fisher or Scientific Products) was charged 366.7 g (1.25 mole) of oxaprozin (Searle Chemical, Augusta, Ga.), and followed by a solution of 154.5 g TRIS in 700 ml water. The resulting mixture was heated to 60° C. (using electric heating mantle), and 1.75 liter isopropanol was added. While maintaining constant volume, 6.5 liter of isopropanol was added gradually as an equivalent volume of liquid was distilled from the system. This process removes the water azeotropically from the flask. Subsequently, the mixture was allowed to cool to 10° C., then stirred for 30 minutes. The mixture was vacuum filtered on a Buchner funnel fitted with Whatman #4 paper, washed twice with 250 ml of isopropanol, and dried at 60° C. in a laboratory forced air dryer. This procedure produced 499.2 g of oxaprozin TRIS salt.

Analysis Calculated for $C_{22}H_{26}N_2O_6$.: C, 63.75; H, 6.32; N, 6.76; 0, 23.17 Found: C, 63.61; H, 6.34; N, 6.76

EXAMPLE 5

Dissolution Rates of the Most Preferred Potassium Salt Tablet Formulation for Oxaprozin Using Different Quantities of Magnesium Stearate I. Formulations Employed in Dissolution Experiments
A. Control Formulation - The control formulation employed was the most preferred potassium salt tablet formulation for oxaprozin
(containing no magnesium stearate)

|  | g/Batch* | % Composition |
|---|---|---|
| Potassium Salt of Oxaprozin | 1356.42 g | 82.71% |
| Pregelatinized Corn Starch | 34.78 g | 2.12% |
| Microcrystalline Cellulose NF | 208.8 g | 12.73% |
| Stearic Acid NF | 32.0 g | 1.95% |
| Colloidal Silicon Dioxide NF | 8.0 g | 0.49% |
| Total | 1,640.0 g | 100.00% |

*(2000 Tablets, 820 mg/Tablet)

B. Test Formulations -
T-1, T-2, T-3 and T-4 are four different potassium salt tablet formulations for oxaprozin which vary the amount of magnesium stearate employed in the formulation, as shown below.

|  | T-1 | T-2 | T-3 | T-4 |
|---|---|---|---|---|
| Potassium Salt of Oxaprozin | 1,356.42 g | 1,356.42 g | 1,356.42 g | 1,356.42 g |
| Pregelatinized Corn Starch | 34.78 g | 34.78 g | 34.78 g | 34.78 g |
| Microcrystalline Cellulose NF | 236.8 g | 232.8 g | 224.8 g | 208.8 g |
| Magnesium Stearate | 4.0 g | 8.0 g | 16.0 g | 32.0 g |
| Colloidal Silicon Dioxide NF | 8.0 g | 8.0 g | 8.0 g | 8.0 g |
| Total (2000 Tablets, 820 mg/Tab | 1,640.0 g | 1,640.0 g | 1,640.0 g | 1,640.0 g |
| % of Magnesium Stearate of the total | 0.244% | 0.488% | 0.976% | 1.952% |

II. Dissolution Experiments

Dissolution experiments were performed in the manner described in Example 1 in order to determine the percentage of a tablet formulation dissolved (control, T-1, T-2, T-3 or T-4) at a given time period (10, 15, 20 30, 45 or 60 minutes) using a wavelength of 286 nm and a concentration of 0.6 mg/ml. Each experiment was performed six times. The data presented in each of these dissolution experiments shows the percentage of tablets dissolved at a given time interval.

A. Control Sample Results (No Magnesium Stearate Employed)

| PERCENT DISSOLVED DATA FOR CONTROL (%) | | | | | | | | | |
|---|---|---|---|---|---|---|---|---|---|
| VESSEL NO. TIME (minutes) | 1 | 2 | 3 | 4 | 5 | 6 | Mean | Standard Deviation | % RSD |
| 10 | 71.0 | 67.6 | 71.5 | 69.9 | 72.5 | 69.1 | 70.3 | 1.8 | 2.5 |
| 15 | 91.1 | 87.6 | 90.8 | 89.9 | 91.8 | 89.1 | 90.0 | 1.5 | 1.7 |
| 20 | 101.2 | 98.4 | 100.2 | 99.7 | 101.1 | 99.1 | 99.9 | 1.1 | 1.1 |
| 30 | 103.0 | 101.5 | 101.6 | 102.0 | 102.5 | 100.7 | 101.9 | 0.8 | 0.8 |
| 45 | 103.0 | 101.6 | 101.7 | 102.1 | 102.7 | 100.9 | 102.0 | 0.8 | 0.7 |
| 60 | 102.9 | 101.6 | 101.3 | 101.8 | 102.7 | 100.7 | 101.8 | 0.8 | 0.8 |

The data presented above show that approximately 70% of the control tablets (containing no magnesium stearate) dissolved after 10 minutes, and that the tablets were completely dissolved after about 20 minutes.

B. T-1 Sample Results (0.244% Magnesium Stearate Employed)

| PERCENT DISSOLVED DATA FOR T-1 (%) | | | | | | | | | |
|---|---|---|---|---|---|---|---|---|---|
| VESSEL NO. TIME (minutes) | 1 | 2 | 3 | 4 | 5 | 6 | Mean | Standard Deviation | % RSD |
| 10 | 37.8 | 40.3 | 37.6 | 37.9 | 36.4 | 34.4 | 37.4 | 1.9 | 5.2 |
| 15 | 55.1 | 53.8 | 52.9 | 55.5 | 53.8 | 49.7 | 53.5 | 2.1 | 3.9 |
| 20 | 70.0 | 63.2 | 67.4 | 70.2 | 68.8 | 64.7 | 67.4 | 2.9 | 4.2 |
| 30 | 89.4 | 80.7 | 88.1 | 90.1 | 89.2 | 85.4 | 87.2 | 3.6 | 4.1 |
| 45 | 100.2 | 98.1 | 100.1 | 100.1 | 101.0 | 99.2 | 99.8 | 1.0 | 1.0 |
| 60 | 100.4 | 100.3 | 100.5 | 100.2 | 100.7 | 99.3 | 100.2 | 0.5 | 0.5 |

The data presented above show that only 37.4% of the T-1 tablets (containing 0.244% magnesium stearate) dissolved after 10 minutes, and that the tablets did not completely dissolve until after more than 45 minutes.

C. T-2 Sample Results (0.488% Magnesium Stearate Employed)

| PERCENT DISSOLVED DATA FOR T-2(%) | | | | | | | | | |
|---|---|---|---|---|---|---|---|---|---|
| VESSEL NO. TIME (minutes) | 1 | 2 | 3 | 4 | 5 | 6 | Mean | Standard Deviation | % RSD |
| 10 | 26.6 | 32.5 | 30.4 | 30.1 | 28.1 | 30.9 | 29.8 | 2.1 | 7.1 |
| 15 | 38.1 | 46.4 | 45.7 | 45.2 | 43.2 | 47.2 | 44.3 | 3.3 | 7.5 |
| 20 | 49.3 | 63.2 | 60.6 | 60.9 | 59.2 | 61.4 | 59.1 | 4.9 | 8.4 |
| 30 | 72.0 | 85.7 | 82.9 | 84.4 | 83.1 | 85.1 | 82.2 | 5.1 | 6.2 |
| 45 | 95.7 | 100.6 | 97.7 | 99.6 | 98.8 | 100.4 | 98.8 | 1.9 | 1.9 |
| 60 | 100.2 | 102.2 | 98.7 | 101.1 | 99.8 | 101.0 | 100.5 | 1.2 | 1.2 |

The data presented above show that only 29.8% of the T-2 tablets (containing 0.488% magnesium stearate) dissolved after 10 minutes, and that the tablets did not completely dissolve until after more than 45 minutes.

D. T-3 Sample Results (0.976% Magnesium Stearate Employed)

PERCENT DISSOLVED DATA FOR T-3(%)

| VESSEL NO. TIME (minutes) | 1 | 2 | 3 | 4 | 5 | 6 | Mean | Standard Deviation | % RSD |
|---|---|---|---|---|---|---|---|---|---|
| 10 | 17.6 | 18.8 | 19.5 | 18.9 | 19.4 | 17.6 | 18.6 | 0.8 | 4.5 |
| 15 | 23.8 | 26.2 | 28.1 | 26.5 | 27.7 | 24.8 | 26.1 | 1.6 | 6.3 |
| 20 | 31.5 | 35.4 | 36.8 | 36.5 | 36.4 | 35.1 | 35.3 | 2.0 | 5.6 |
| 30 | 50.2 | 60.5 | 56.7 | 56.9 | 58.7 | 60.9 | 57.3 | 3.9 | 6.8 |
| 45 | 81.9 | 86.7 | 85.0 | 85.2 | 81.0 | 87.0 | 84.5 | 2.5 | 2.9 |
| 60 | 97.5 | 99.3 | 98.9 | 97.9 | 98.6 | 99.0 | 98.5 | 0.7 | 0.7 |

The data presented above show that only 18.6% of the T-3 tablets (containing 0.976% of magnesium stearate) dissolved after 10 minutes, and that the tablets did not completely dissolve until after more than 1 hour.

E. T-4 Sample Results (1.952% Magnesium Stearate Employed)

PERCENT DISSOLVED DATA FOR T-4(%)

| VESSEL NO. TIME (minutes) | 1 | 2 | 3 | 4 | 5 | 6 | Mean | Standard Deviation | % RSD |
|---|---|---|---|---|---|---|---|---|---|
| 10 | 16.6 | 13.6 | 15.1 | 15.8 | 15.1 | 15.6 | 15.3 | 1.0 | 6.5 |
| 15 | 21.2 | 17.1 | 19.3 | 20.4 | 19.2 | 20.1 | 19.5 | 1.4 | 7.2 |
| 20 | 29.2 | 25.3 | 29.5 | 32.5 | 34.6 | 35.2 | 31.0 | 3.8 | 12.1 |
| 30 | 38.7 | 32.0 | 38.9 | 39.5 | 37.8 | 38.6 | 37.6 | 2.8 | 7.5 |
| 45 | 63.9 | 50.2 | 68.3 | 67.1 | 66.3 | 65.0 | 63.5 | 6.7 | 10.5 |
| 60 | 86.1 | 70.7 | 86.9 | 86.1 | 86.4 | 85.1 | 83.5 | 6.3 | 7.6 |

The data presented above show that only 15.3% of the T-4 tablets (containing 1.952% magnesium stearate) dissolved after 10 minutes, and that the tablets did not completely dissolve until after more than 1 hour.

EXAMPLE 6

Variation of Active Concentration

In this experiment, different sized tablets containing the same ingredients, and the same % weight of the total tablet weight, were made, and then the dissolution of those tablets was evaluated in the manner described in Example 1. The tablets each contained the ingredients, and % weight of the total tablet weight, listed hereinbelow. The six different sized tablets contained the number of milligrams listed hereinbelow under the table heading of Total Tablet Weight.

Unless described differently, the tablets employed in this study were prepared in the manner described hereinabove in Example 2. The tablets were compressed in a manner known by those of skill in the art at six different total tablet weights to yield tablets of the different active concentrations described hereinbelow.

| Formulation for Potassium Oxaprozin Core Tablets (Not Coated) | |
|---|---|
| Component | % Weight of the Total Tablet |
| Potassium Salt of Oxaprozin | 82.67% |
| Pregelatinized Corn Starch, NF | 2.16% |
| Water, USP | 0% |
| Colloidal Silicon Dioxide, NF | 0.49% |
| Microcrystalline Cellulose, NF | 12.73% |
| Stearic Acid, NF | 1.95% |
| Total | 100.00% |
| TOTAL TABLET WEIGHT | OXAPROZIN CONTENT |
| 273.4 mg/tablet | 200.0 mg Activity |
| 546.7 mg/tablet | 400.0 mg Activity |
| 820.0 mg/tablet | 600.0 mg Activity |
| 1093.5 mg/tablet | 800.0 mg Activity |
| 1366.9 mg/tablet | 1000.0 mg Activity |
| 1640.0 mg/tablet | 1200.0 mg Activity |

The dissolution data obtained from this experiment is presented below, and shows the percentage of the tablets dissolved at different time intervals. Dissolution of the tablets was tested in the manner described in Example 1.

| | | Dissolution Data (Mean Dissolution Data, n = 6) | | | | | |
|---|---|---|---|---|---|---|---|
| | | 10 Min | 15 Min | 20 Min | 30 Min | 45 Min | 60 Min |
| 200 mg | Conc. % | 81.5% | 95.2% | 97.4% | 97.2% | 97.1% | 97.0% |
| Activity | StdDev | 3.028 | 1.460 | 1.099 | 0.673 | 0.808 | 0.887 |
| 400 mg | Conc. % | 69.8% | 87.5% | 96.8% | 99.4% | 99.4% | 99.4% |
| Activity | StdDev | 3.885 | 3.983 | 3.482 | 2.709 | 2.748 | 2.846 |
| 600 mg | Conc. % | 69.0% | 88.0% | 97.4% | 99.3% | 99.4% | 99.4% |
| Activity | StdDev | 1.726 | 1.569 | 1.065 | 1.250 | 1.294 | 1.295 |
| 800 mg | Conc. % | 66.4% | 84.6% | 95.4% | 100.2% | 100.4% | 100.4% |
| Activity | StdDev | 1.563 | 1.741 | 1.569 | 1.256 | 1.384 | 1.129 |
| 1000 mg | Conc. % | 57.6% | 76.1% | 88.5% | 90.3% | 98.0% | 97.9% |
| Activity | StdDev | 2.874 | 2.706 | 1.848 | 1.886 | 1.328 | 1.284 |
| 1200 mg | Conc. % | 53.5% | 70.5% | 82.7% | 95.4% | 96.9% | 96.9% |
| Activity | StdDev | 3.134 | 2.483 | 2.098 | 1.775 | 1.385 | 1.543 |

As the data presented above shows, all six of the different weight tablet formulations described above were successfully dissolved in the dissolution media. While the formulations compressed well, and there was no evidence of sticking to the mechanical press, as total tablet weight increased, more pressure was needed for compression of the tablets to prevent sticking. As a result, the larger the tablet, the harder the tablet became. This was probably not of significance because all six types of tablets had acceptable disintegrations (7 to 18 minutes). All dissolution testing gave acceptable results (average greater than 90% at 30 minutes).

EXAMPLE 7

Variation of Excipient Concentration

In this experiment, the amount of each of the ingredients of the formulation for the potassium oxaprozin core tablets described in Example 2 was varied, and then dissolution testing was conducted for each of the 30 formulations made. All of these formulations were prepared in the manner described in Example 2, and the various excipients were added at the levels indicated in the table presented below. The 30 formulations tested were made in small quantities (approximately two kilos).

| | Percentage Ingredient Employed of the Total Tablet Weight for 30 Different Formulations | | | | | | |
|---|---|---|---|---|---|---|---|
| Form. No. | Tablet Weight (Mg) | % K OXA | % MC | % CS | % SA | % CD | Total |
| 1 | 722.9 mg | 70.44% | 20.78% | 3.82% | 4.16% | 0.80% | 100.0% |
| 2 | 779.9 mg | 65.28% | 19.26% | 9.65% | 3.85% | 1.96% | 100.0% |
| 3 | 1183.4 mg | 66.83% | 25.35% | 4.44% | 1.69% | 1.69% | 100.0% |
| 4 | 1193.8 mg | 66.24% | 25.13% | 4.40% | 3.35% | 0.88% | 100.0% |
| 5 | 608.9 mg | 37.14% | 49.29% | 8.55% | 3.29% | 1.73% | 100.0% |
| 6 | 1738.8 mg | 77.98% | 17.25% | 3.02% | 1.15% | 0.60% | 100.0% |
| 7 | 1070.4 mg | 47.54% | 42.08% | 7.03% | 2.81% | 0.54% | 100.0% |
| 8 | 873.8 mg | 90.50% | 0.0% | 6.01% | 2.29% | 1.20% | 100.0% |
| 9 | 1002.9 mg | 50.75% | 44.92% | 2.76% | 1.0% | 0.57% | 100.0% |
| 10 | 1164.3 mg | 67.92% | 25.76% | 4.51% | 1.72% | 0.09% | 100.0% |
| 11 | 1297.3 mg | 82.73% | 11.56% | 2.22% | 2.31% | 1.18% | 100.0% |
| 12 | 1059.9 mg | 48.02% | 42.50% | 7.10% | 0.94% | 1.44% | 100.0% |
| 13 | 1173.8 mg | 67.37% | 25.56% | 4.47% | 1.70% | 0.90% | 100.0% |
| 14 | 1126.3 mg | 70.22% | 26.63% | 0.44% | 1.78% | 0.93% | 100.0% |
| 15 | 1221.3 mg | 64.84% | 24.60% | 8.06% | 1.64% | 0.86% | 100.0% |
| 16 | 1587.8 mg | 67.60% | 28.34% | 1.81% | 1.89% | 0.36% | 1o0.0% |
| 17 | 1324.8 mg | 81.16% | 11.34% | 5.59% | 0.76% | 1.15% | 100.0% |
| 18 | 1473.8 mg | 53.66% | 40.71% | 3.56% | 1.36% | 0.71% | 100.0% |
| 19 | 1173.8 mg | 67.37% | 25.56% | 4.47% | 1.70% | 0.90% | 100.0% |
| 20 | 750.4 mg | 67.85% | 20.02% | 10.03% | 1.33% | 0.77% | 100.0% |
| 21 | 1173.8 mg | 67.37% | 25.56% | 4.47% | 1.70% | 0.90% | 100.0% |
| 22 | 1577.3 mg | 68.05% | 28.53% | 1.82% | 0.63% | 0.97% | 100.0% |
| 23 | 1644.8 mg | 65.25% | 27.36% | 4.64% | 1.82% | 0.93% | 100.0% |
| 24 | 1153.8 mg | 68.54% | 26.00% | 4.55% | 0.00% | 0.91% | 100.0% |
| 25 | 1267.8 mg | 84.66% | 11.83% | 2.27% | 0.79% | 0.45% | 100.0% |
| 26 | 1173.8 mg | 67.37% | 25.56% | 4.47% | 1.70% | 0.90% | 100.0% |
| 27 | 1032.4 mg | 49.29% | 43.64% | 2.68% | 2.91% | 1.48% | 100.0% |
| 28 | 1335.3 mg | 80.38% | 11.23% | 5.71% | 2.25% | 0.43% | 100.0% |
| 29 | 1615.3 mg | 66.45% | 27.85% | 4.72% | 0.62% | 0.36% | 100.0% |
| 30 | 712.4 mg | 71.37% | 21.05% | 4.04% | 1.40% | 2.14% | 100.0% |

The dissolution data obtained from the testing of these 30 formulations is presented below, and shows the percentage of the tablets dissolved over different time intervals. Dissolution was tested in the manner described in Example 1.

These formulations were individually prepared on a small scale, following the procedure described in Example 2.

The individual formulas produced in this experiment were as follows:

Dissolution Data
(Mean Dissolution Data, n = 6)

| Form No | 10 Min | SD | 15 Min | SD | 20 Min | SD | 30 Min | SD | 45 Min | SD | 60 Min | SD |
|---|---|---|---|---|---|---|---|---|---|---|---|---|
| 1 | 57.3% | 0.996 | 77.2% | 1.436 | 91.6% | 1.849 | 102.5% | 2.370 | 101.4% | 2.247 | 102.2% | 2.214 |
| 2 | 49.7% | 0.714 | 69.4% | 1.096 | 84.9% | 0.995 | 101.4% | 1.092 | 102.0% | 1.303 | 102.0% | 1.356 |
| 3 | 43.7% | 2.032 | 61.9% | 1.788 | 76.3% | 1.865 | 94.1% | 1.725 | 99.2% | 1.746 | 99.1% | 1.693 |
| 4 | 42.9% | 2.037 | 60.4% | 2.331 | 75.0% | 1.904 | 93.2% | 0.480 | 99.2% | 1.828 | 99.2% | 1.786 |
| 5 | 32.2% | 1.893 | 48.3% | 2.318 | 65.1% | 2.752 | 95.8% | 4.059 | 106.9% | 4.322 | 107.1% | 4.168 |
| 6 | 48.3% | 0.911 | 65.0% | 1.316 | 78.0% | 1.525 | 93.5% | 1.496 | 98.4% | 0.631 | 98.5% | 0.789 |
| 7 | 36.8% | 1.859 | 53.8% | 2.858 | 68.7% | 2.929 | 92.1% | 3.894 | 100.2% | 1.898 | 99.7% | 1.931 |
| 8 | 66.6% | 2.025 | 85.6% | 1.186 | 95.9% | 0.611 | 98.4% | 0.880 | 98.3% | 0.952 | 98.4% | 1.028 |
| 9 | 32.0% | 2.132 | 39.2% | 1.812 | 53.5% | 4.366 | 69.1% | 1.318 | 92.4% | 1.928 | 101.6% | 1.359 |
| 10 | 47.5% | 1.754 | 65.9% | 1.620 | 80.2% | 1.352 | 97.2% | 1.288 | 99.6% | 1.408 | 99.5% | 1.460 |
| 11 | 61.8% | 2.147 | 79.7% | 1.755 | 91.0% | 1.550 | 97.8% | 1.383 | 97.8% | 1.530 | 97.8% | 1.562 |
| 12 | 31.6% | 1.744 | 47.3% | 1.897 | 61.6% | 2.199 | 84.3% | 2.562 | 100.2% | 1.189 | 100.4% | 1.280 |
| 13 | 43.9% | 2.122 | 61.2% | 2.850 | 74.9% | 2.593 | 93.0% | 2.117 | 101.9% | 1.140 | 102.1% | 1.047 |
| 14 | 55.1% | 1.055 | 74.6% | 0.869 | 88.6% | 0.551 | 100.5% | 1.171 | 100.4% | 1.352 | 100.3% | 1.321 |
| 15 | 47.4% | 2.299 | 63.4% | 1.880 | 78.8% | 1.650 | 97.9% | 1.765 | 103.2% | 1.794 | 103.3% | 1.837 |
| 16 | 35.5% | 1.306 | 49.7% | 1.235 | 61.7% | 1.252 | 79.4% | 2.003 | 95.2% | 1.852 | 98.4% | 2.167 |
| 17 | 59.9% | 2.736 | 79.5% | 2.353 | 91.9% | 1.256 | 99.7% | 0.965 | 99.7% | 1.005 | 99.5% | 0.933 |
| 18 | 19.0% | 1.319 | 27.5% | 1.156 | 35.8% | 1.269 | 51.3% | 2.299 | 73.1% | 3.279 | 84.9% | 3.457 |
| 19 | 42.4% | 1.796 | 58.7% | 1.902 | 72.3% | 2.027 | 91.3% | 1.507 | 100.8% | 0.939 | 100.8% | 1.015 |
| 20 | 65.8% | 1.782 | 87.2% | 2.460 | 100.4% | 2.904 | 104.1% | 2.769 | 104.3% | 2.651 | 103.9% | 2.969 |
| 21 | 42.3% | 1.904 | 58.3% | 2.366 | 71.7% | 2.509 | 90.3% | 2.923 | 99.7% | 1.774 | 100.0% | 1.481 |
| 22 | 32.7% | 1.825 | 46.3% | 2.129 | 57.7% | 2.456 | 75.4% | 3.647 | 91.8% | 3.444 | 95.7% | 2.485 |
| 23 | 28.7% | 2.205 | 40.3% | 2.605 | 51.2% | 3.147 | 69.5% | 4.540 | 87.1% | 4.219 | 96.3% | 4.058 |
| 24 | 53.3% | 3.284 | 71.5% | 2.694 | 83.1% | 2.032 | 99.5% | 2.273 | 100.3% | 2.491 | 100.4% | 2.463 |
| 25 | 63.9% | 5.212 | 82.6% | 4.495 | 93.5% | 2.963 | 98.4% | 1.035 | 98.5% | 0.998 | 98.4% | 0.913 |
| 26 | 40.7% | 1.072 | 56.9% | 1.296 | 69.8% | 1.449 | 88.5% | 1.420 | 97.3% | 0.717 | 97.4% | 0.646 |
| 27 | 25.8% | 1.362 | 36.7% | 1.936 | 47.7% | 2.499 | 67.7% | 3.551 | 90.4% | 4.036 | 99.1% | 1.593 |
| 28 | 59.7% | 3.272 | 78.9% | 3.090 | 91.3% | 2.610 | 100.2% | 1.268 | 100.4% | 1.236 | 100.4% | 1.247 |
| 29 | 32.9% | 2.386 | 46.0% | 2.586 | 57.7% | 3.055 | 75.6% | 3.895 | 92.8% | 3.909 | 97.7% | 4.197 |
| 30 | 61.5% | 1.010 | 82.1% | 1.090 | 95.2% | 1.273 | 100.6% | 1.600 | 100.3% | 1.522 | 100.2% | 1.635 |

It was observed during this experiment that the tablets do not really disintegrate, but they appear to erode slowly or dissolve.

It was also observed during this experiment that, when the level of stearic acid drops below 1%, the formulations become more difficult to produce because side wall scoring takes place, and the formulations encounter more difficulty releasing from a mechanical press. This is best seen in formulation number 24, where the stearic acid was removed completely, and in formulations numbers 22 and 29. Formulation number 24 was terminated after enough tablets were produced to supply for testing. The reason was that side wall scoring and ejection problems were occurring. Thus, it may be concluded that the above-tested formulations of the present invention which contain less than 1% of stearic acid would be less desirable for production on a commercial scale.

EXAMPLE 8

Active Ingredient Replacement

In this experiment, the active ingredient potassium oxaprozin was replaced with two different active compounds, sodium oxaprozin and Tris oxaprozin.

SODIUM OXAPROZIN

|  | Mg/Tablet | % Weight of the Total Tablet |
|---|---|---|
| Sodium Oxaprozin | 645.2 mg | 82.0% |
| Corn Starch | 17.7 mg | 2.2% |
| Microcrystalline Cellulose | 104.4 mg | 13.3% |
| Silicon Dioxide | 4.0 mg | 0.5% |
| Stearic Acid | 16.0 mg | 2.0% |
| Total | 787.3 mg | 100.0% |

|  | Mg/Tablet | % Weight of the Total Tablet |
|---|---|---|
| Tris Oxaprozin | 847.9 mg | 85.6% |
| Corn Starch | 17.7 mg | 1.8% |
| Microcrystalline Cellulose | 104.4 mg | 10.6% |

-continued

|  | Mg/Tablet | % Weight of the Total Tablet |
|---|---|---|
| Silicone Dioxide | 4.0 mg | 0.4% |
| Stearic Acid | 16.0 mg | 1.6% |
| Total | 990.0 mg | 100.0% |

The granulation and tablet compression with both of the above formulations was successful.

The Tris oxaprozin material seemed to be much more soluble than the potassium oxaprozin. This made the granulation step more difficult due to the lesser amount of water needed. The granulation became over wet and stuck to the sides of the granulator. The problem was overcome by wet screening the formulation through a Friewitt oscillating granulator (Key International, Inc., Englishtown, N.J.) in a manner known by those of skill in the art before fluid bed drying. The compression of the tablets showed some evidence of sticking. This can be corrected by increasing the force of compression or slightly adjusting the formulation by adding more lubricant or anti-adherent.

The sodium oxaprozin granulation also required wet screening, but was not as difficult to prepare. Some over wetting also occurred. The tabletting portion of the sodium oxaprozin trial was good. The tablets ran well, and had no evidence of sticking at low compression forces. The weights of the individual tablets were not difficult to control.

Dissolution of the two above-described formulations was tested in the manner described in Example 1, and shows the percentage of the tablets dissolved at different time intervals. Dissolution results for both active ingredient replacements performed are presented in the table below. It can be seen that greater than 95% of the tablets of the two different formulations dissolved in 30 minutes.

Dissolution Data
(Mean Dissolution Data, n = 6)

|  |  | 10 Min | 15 Min | 20 Min | 30 Min | 45 Min | 60 Min |
|---|---|---|---|---|---|---|---|
| Tris Oxaprozin | Conc. | 51.4% | 69.7% | 83.4% | 95.6% | 96.0% | 96.0% |
|  | StdDev | 2.286 | 3.035 | 3.072 | 1.909 | 1.899 | 1.834 |
| Sodium Oxaprozin | Conc. | 59.5% | 81.4% | 93.3% | 96.3% | 96.3% | 96.4% |
|  | StdDev | 8.149 | 9.220 | 6.555 | 0.612 | 0.660 | 0.612 |

EXAMPLE 9

Excipient Replacement

In this experiment, the excipients employed in the potassium oxaprozin formulation described in Example 2 were replaced with other excipients by class of function. The classes of excipients examined were as follows:

(1) Glidants (2) Anti-adherents (3) Binders (4) Fillers (Water Insoluble and Water Soluble)

(5) Lubricants (Water Insoluble and Water Soluble)

No other changes were made to the formulation.

The results of this experiment are summarized in pairs because each excipient which is present in the formulation described in Example 2 was replaced with two alternate excipients from the same class. In all cases, the formulations made in this experiment were made in the manner described in Example 2. The dissolution data obtained from the testing of these different formulations is presented in the various tables appearing hereinbelow, and show the percentage of the tablets dissolved over different time intervals. Dissolution was tested in the manner described in Example 1.

(1) Glidants

The first two trials removed the glidant, colloidal silicon dioxide and replaced it with either talc or corn starch. The formulations produced in these trials were as follows:

| Ingredients | Mg/Tablet | % of Composition |
|---|---|---|
| Colloidal Silicon Dioxide Replaced with Talc | | |
| Potassium Oxaprozin | 677.9 mg | 79.2% |
| Pregelatinized Starch | 17.4 mg | 2.0% |
| Microcrystalline Cellulose | 104.4 mg | 12.2% |
| Stearic Acid | 16.0 mg | 1.9% |
| Talc | 40.3 mg | 4.7% |
|  | 856.0 mg | 100.0% |
| Colloidal Silicon Dioxide Replaced with Corn Starch | | |
| Potassium Oxaprozin | 677.9 mg | 77.3% |
| Pregelatinized Starch | 17.4 mg | 2.0% |
| Microcrystalline Cellulose | 104.4 mg | 11.9% |
| Stearic Acid | 16.0 mg | 1.8% |

-continued

| Ingredients | Mg/Tablet | % of Composition |
|---|---|---|
| Corn Starch | 61.3 mg | 7.0% |
|  | 877.0 mg | 100.0% |

The talc level was 4.7% w/w (4.7% of the total tablet weight) and the corn starch level was 7.0% w/w. Both of the trials were successful in making tablets which meet the criteria described hereinabove. When talc was used, the tablet weights were harder to control, and the flow of the granulation in the tablet machine appeared to be hindered. The corn starch performed better, and the problems encountered with talc were not observed.

| | | Dissolution Data (Mean Dissolution Data. n = 6) | | | | | |
|---|---|---|---|---|---|---|---|
| | | 10 Min | 15 Min | 20 Min | 30 Min | 45 Min | 60 Min |
| Talc | Conc. | 68.5% | 86.7% | 96.9% | 98.6% | 98.8% | 98.8% |
| | StdDev | 1.166 | 1.195 | 1.222 | 1.444 | 1.510 | 1.474 |
| Corn Starch | Conc. | 71.8% | 90.7% | 99.2% | 100.3% | 100.5% | 100.5% |
| | StdDev | 1.388 | 0.773 | 0.536 | 0.669 | 0.583 | 0.537 |

The results of the dissolution testing show that replacing the colloidal silicon dioxide with talc or corn starch does not adversely affect the rate of dissolution. Dissolution experiments performed with each of these formulations showed greater than 98% tablet dissolution at the thirty minute interval.

(2) Anti-Adherents

The second two trials removed the anti-adherent colloidal silicon dioxide and replaced it with either magnesium stearate or sodium laurel sulfate. The formulations produced in these trials were as follows:

| Ingredients | Mg/Tablet | % of Composition |
|---|---|---|
| Colloidal Silicon Dioxide Replaced with Magnesium Stearate | | |
| Potassium Oxaprozin | 677.9 mg | 82.7% |
| Pregelatinized Starch | 17.4 mg | 2.1% |
| Microcrystalline Cellulose | 104.4 mg | 12.7% |
| Stearic Acid | 16.0 mg | 2.0% |
| Magnesium Stearate | 4.3 mg | 0.5% |
| | 820.0 mg | 100.0% |
| Colloidal Silicon Dioxide Replaced with Sodium Laurel Sulfate | | |
| Potassium Oxaprozin | 677.9 mg | 82.6% |
| Pregelatinized Starch | 17.4 mg | 2.1% |
| Microcrystalline Cellulose | 104.4 mg | 12.7% |
| Stearic Acid | 16.0 mg | 2.0% |
| Sodium Laurel Sulfate | 4.3 mg | 0.5% |
| | 820.0 mg | 100.0% |

In both cases, the replacement level of the anti-adherent was 0.5% w/w (0.5% of the total tablet weight). No problems were encountered with either of these trials, the tablet weights were easy to control and the flow of the granulation in the tablet machine was good. There was no evidence of sticking of the tablets to the mechanical press.

The results of dissolution testing show that the above-described replacements did not adversely affect the dissolution. Dissolution experiments performed with each of these formulations showed almost 100.0% tablet dissolution at the thirty minute time interval.

(3) Binders

The third two trials removed the binder corn starch and replaced it with either sucrose or polyvinylpyrrolidone (PVP). The formulations produced in these trials were as follows:

| Ingredients | Mg/Tablet | % of Composition |
|---|---|---|
| Corn Starch Replaced with Sucrose | | |
| Potassium Oxaprozin | 677.9 mg | 81.2% |
| Sucrose | 31.9 mg | 3.8% |
| Microcrystalline Cellulose | 104.4 mg | 12.5% |
| Silicon Dioxide | 4.0 mg | 0.5% |
| Stearic Acid | 16.0 mg | 2.0% |
| | 834.2 mg | 100.0% |
| Corn Starch Replaced with PVP | | |
| Potassium Oxaprozin | 677.9 mg | 82.8% |
| PVP (Polyvinylpyrolidine) | 16.7 mg | 2.0% |
| Microcrystalline Cellulose | 104.4 mg | 12.7% |
| Silicon Dioxide | 4.0 mg | 0.5% |
| Stearic Acid | 16.0 mg | 2.0% |
| | 819.0 mg | 100.0% |

The sucrose level was 3.8% w/w (3.8% of the total tablet weight) and the PVP level was 2.0% w/w (2% of the total tablet weight). With respect to both of the replacements, the trials granulated well, compressed well in the tablet press, tablet weights and flow of the formulations through the tablet machine were good and there was no evidence of sticking.

| | | Dissolution Data (Mean Dissolution Data, n = 6) | | | | | |
|---|---|---|---|---|---|---|---|
| | | 10 Min | 15 Min | 20 Min | 30 Min | 45 Min | 60 Min |
| Magnesium Stearate | Conc. | 50.1% | 69.2% | 83.7% | 97.5% | 98.5% | 98.3% |
| | StdDev | 1.112 | 1.297 | 1.291 | 0.772 | 0.296 | 0.179 |
| Sodium Laurel Sulfate | Conc. | 69.4% | 88.8% | 97.8% | 99.2% | 99.2% | 99.2% |
| | StdDev | 1.180 | 1.059 | 0.987 | 0.678 | 0.745 | 0.753 |

| | | Dissolution Data | | | | | |
|---|---|---|---|---|---|---|---|
| | | (Mean Dissolution Data, n = 6) | | | | | |
| | | 10 Min | 15 Min | 20 Min | 30 Min | 45 Min | 60 Min |
| Sucrose | Conc. | 75.1% | 92.5% | 97.3% | 97.3% | 97.4% | 97.4% |
| | StdDev | 3.874 | 2.624 | 1.554 | 1.543 | 1.568 | 1.550 |
| PVP | Conc. | 70.6% | 89.7% | 98.7% | 99.6% | 99.7% | 99.7% |
| | StdDev | 1.601 | 1.456 | 1.240 | 1.022 | 1.021 | 1.048 |

The results of the dissolution testing showed that replacing the corn starch with either PVP or sucrose did not adversely affect dissolution. The tablet dissolution values at the thirty minute interval for both replacements were in excess of 97.0%.

(4) Fillers (a) Water Insoluble Fillers

The fourth two trials removed the water insoluble filler microcrystalline cellulose and replaced it with either dicalcium phosphate or calcium carbonate, two other water insoluble fillers. The formulations produced in these trials were as follows:

| Ingredients | Mg/Tablet | % of Composition |
|---|---|---|
| Microcrystalline Cellulose Replaced with Calcium Carbonate | | |
| Potassium Oxaprozin | 677.9 mg | 82.7% |
| Pregelatinized Starch | 17.4 mg | 2.1% |
| Calcium Carbonate | 104.7 mg | 12.7% |
| Silicon Dioxide | 4.0 mg | 0.5% |
| Stearic Acid | 16.0 mg | 2.0% |
| | 820.0 mg | 100.0% |
| Microcrystalline Cellulose Replaced with Dicalcium Phosphate | | |
| Potassium Oxaprozin | 677.9 mg | 82.7% |
| Pregelatinized Starch | 17.4 mg | 2.1% |
| Dicalcium Phosphate | 104.7 mg | 12.7% |
| Silicon Dioxide | 4.0 mg | 0.5% |
| Stearic Acid | 16.0 mg | 2.0% |
| | 820.0 mg | 100.0% |

In each case, the replacement was 1:1 (the same mg of the water insoluble filler was employed). Each of the formulations was compressed easily in the tablet press, and there was no evidence of sticking to the press.

The results of dissolution testing showed that replacing microcrystalline cellulose with either dicalcium phosphate or calcium carbonate would not meet the criteria described hereinabove.

(b) Water Soluble Fillers

The fifth two trials removed the water insoluble filler, microcrystalline cellulose and replaced it with either sucrose or lactose, both of which are water soluble fillers. The formulations produced in these trials were as follows:

| Ingredients | Mg/Tablet | % of Composition |
|---|---|---|
| Microcrystalline Cellulose Replaced with Lactose | | |
| Potassium Oxaprozin | 677.9 mg | 82.7% |
| Pregelatinized Starch | 17.4 mg | 2.1% |
| Lactose | 104.7 mg | 12.7% |
| Silicon Dioxide | 4.0 mg | 0.5% |
| Stearic Acid | 16.0 mg | 2.0% |
| | 820.0 mg | 100.0% |
| Microcrystalline Cellulose Replaced with Sucrose | | |
| Potassium Oxaprozin | 677.9 mg | 82.7% |
| Pregelatinized Starch | 17.4 mg | 2.1% |
| Sucrose | 104.7 mg | 12.7% |
| Silicon Dioxide | 4.0 mg | 0.5% |
| Stearic Acid | 16.0 mg | 2.0% |
| | 820.0 mg | 100.0% |

In both cases, the replacement was 1:1. The tablets compressed easily in the tablet press, and the appearance of each of the two sets of tablets was improved due to a shine which was present. Tablet weights and flow of the formulations through the tablet machines were good, and there was no evidence of sticking of any tablets to the tablet press.

| | | Dissolution Data | | | | | |
|---|---|---|---|---|---|---|---|
| | | (Mean Dissolution Data, n = 6) | | | | | |
| | | 10 Min | 15 Min | 20 Min | 30 Min | 45 Min | 60 Min |
| Dicalcium | Conc. | 1.2% | 1.7% | 3.1% | 4.5% | 12.0% | 27.2% |
| phosphate | StdDev | 0.160 | 0.139 | 1.806 | 0.494 | 2.196 | 8.374 |
| Calcium | Conc. | 24.8% | 31.4% | 36.7% | 46.9% | 57.8% | 65.5% |
| carbonate | StdDev | 2.202 | 3.275 | 4.591 | 7.807 | 11.595 | 13.251 |

| | | Dissolution Data (Mean Dissolution Data, n = 6) | | | | | |
|---|---|---|---|---|---|---|---|
| | | 10 Min | 15 Min | 20 Min | 30 Min | 45 Min | 60 Min |
| Sucrose | Conc. | 76.7% | 94.3% | 99.3% | 99.5% | 99.9% | 99.8% |
| | StdDev | 2.808 | 1.869 | 0.376 | 0.699 | 0.653 | 0.631 |
| Lactose | Conc. | 72.5% | 92.2% | 99.8% | 100.0% | 99.9% | 100.1% |
| | StdDev | 1.719 | 1.369 | 0.743 | 0.337 | 0.539 | 0.232 |

The dissolution results for both of these formulations showed that the dissolution was slightly enhanced by both types replacement. The percentage of the tablet dissolved at the thirty minute interval for each type of replacement was greater than 99.5%.

(6) Lubricants

The lubricant replacement portion of the study consisted of four trials. In all cases, the trials were performed with formulations in which the stearic acid had been removed and replaced with either a water insoluble lubricant or a water soluble lubricant.

(a) Water Insoluble Lubricants

The first water insoluble lubricant replacement trial removed the stearic acid and replaced it with the water insoluble lubricant calcium stearate. The formulation produced in this trial was as follows:

| Stearic Acid Replaced with Calcium Stearate | | |
|---|---|---|
| Ingredients | Mg/Tablet | % of Composition |
| Potassium Oxaprozin | 677.9 mg | 83.9% |
| Pregelatinized Starch | 17.4 mg | 2.2% |
| Microcrystalline Cellulose | 104.4 mg | 12.9% |
| Silicon Dioxide | 4.0 mg | 0.5% |
| Calcium Stearate | 4.3 mg | 0.5% |
| | 808.0 mg | 100.0% |

Although this formulation produced enough tablets for the purpose of the experiment, side wall scrubbing (die ejection problems with the tablet press machine) was occurring. To avoid damage to the tablet machine, only 230 gms of the formulation was compressed into tablets. The level of calcium stearate was 0.5% w/w (0.5% of the total tablet weight).

The second water insoluble lubricant replacement trial removed the stearic acid and replaced it with the water insoluble lubricant hydrogenated castor oil. The formulation produced in this trial was as follows:

| Stearic Acid Replaced with Hydrogenated Castor Oil | | |
|---|---|---|
| Ingredients | Mg/Tablet | % of Composition |
| Potassium Oxaprozin | 677.9 mg | 82.7% |
| Pregelatinized Corn Starch | 17.4 mg | 2.1% |
| Colloidal Silicon Dioxide | 4.0 mg | 0.5% |

| Stearic Acid Replaced with Hydrogenated Castor Oil | | |
|---|---|---|
| Ingredients | Mg/Tablet | % of Composition |
| Microcrystalline Cellulose | 104.4 mg | 12.7% |
| Hydrogenated Castor Oil | 16.3 mg | 2.0% |
| | 820.0 mg | 100.0% |

This trial was terminated due to the sticking of the granulation to the upper and lower punch faces of the tablet machine. The level of hydrogenated castor oil was at 2.0% w/w (2% of the total tablet weight). In an attempt to improve this trial, an additional lubricant (water insoluble) of 2.0% w/w glycerol behenate (Gattefosse, St. Priest, France) was added to this formulation. This formulation still resulted in excessive sticking to the tablet machine. Thus, no dissolution testing was performed with this formulation.

The third water insoluble lubricant replacement trial removed the stearic acid and replaced it with the water insoluble lubricant, talc. The formulation produced in this trial was as follows:

| Stearic Acid Replaced with Talc | | |
|---|---|---|
| Ingredients | Mg/Tablet | % of Composition |
| Potassium Oxaprozin | 677.9 mg | 80.3% |
| Pregelatinized Starch | 17.4 mg | 2.1% |
| Microcrystalline Cellulose | 104.4 mg | 12.3% |
| Silicon Dioxide | 4.0 mg | 0.5% |
| Talc | 40.3 mg | 4.8% |
| | 844.0 mg | 100.0% |

The level of talc used was 4.8% w/w (4.8% of the total tablet weight). In this trial, the tablet weights were easy to control. There was some sticking to the punch faces of the tablet machine, but once a waxy film formed on the punch faces as a result of the granulation having a tendency to stick to the punch faces, the sticking did not worsen.

Dissolution Data
(Mean Dissolution Data, n = 6)

|  |  | 10 Min | 15 Min | 20 Min | 30 Min | 45 Min | 60 Min |
|---|---|---|---|---|---|---|---|
| Calcium | Conc. | 61.3% | 80.7% | 92.6% | 96.1% | 96.7% | 96.8% |
| stearate | StdDev | 2.850 | 2.820 | 2.259 | 0.893 | 1.014 | 0.949 |
| Talc | Conc. | 93.8% | 99.8% | 100.3% | 100.2% | 100.3% | 100.1% |
|  | StdDev | 1.851 | 1.036 | 1.028 | 0.918 | 0.522 | 0.881 |

The dissolution data presented above showed that, in each of the calcium stearate and talc water insoluble lubricant replacement formulations, greater than 96% of the tablets containing these two formulations dissolved in thirty minutes. Due to some difficulty in tabletting experienced with the formulation made with calcium stearate, the use of talc in the formulations of the present invention is preferable to the use of calcium stearate.

(b) Water Soluble Lubricants

The final three replacement experiments removed the stearic acid and replaced it with water soluble lubricants.

The first experiment removed stearic acid and replaced it with sodium laurel sulfate at a 4.0% level w/w (4% of the tablet weight). The formulation produced in this trial was as follows:

Stearic Acid Replaced with Sodium Lauryl Sulfate

| Ingredients | Mg/Tablet | % of Composition |
|---|---|---|
| Potassium Oxaprozin | 677.9 mg | 81.1% |
| Pregelatinized Starch | 17.4 mg | 2.1% |
| Microcrystalline Cellulose | 104.4 mg | 12.5% |
| Silicon Dioxide | 4.0 mg | 0.5% |
| Sodium Lauryl Sulfate | 32.3 mg | 3.3% |
|  | 836.0 mg | 100.0% |

The initial tablets produced stuck to the punches of the tablet machine, but such sticking ceased to occur with increased force of compression used with the tablet machine.

The next replacement experiment removed the stearic acid and replaced it with the water soluble lubricant polyethylene glycol 4600. The formulation produced in this trial was as follows:

Stearic Acid Replaced with PEG 4600

| Ingredients | Mg/Tablet | % of Composition |
|---|---|---|
| Potassium Oxaprozin | 677.9 mg | 81.1% |
| Pregelatinized Starch | 17.4 mg | 2.1% |
| Colloidal Silicon Dioxide | 4.0 mg | 0.5% |
| Microcrystalline Cellulose | 104.4 mg | 12.5% |
| PEG 4600 | 32.3 mg | 3.8% |
|  | 836.0 mg | 100.0% |

This trial resulted in sticking to the punch faces of the tablet machine. In an attempt to diminish this sticking, polyethylene glycol 8000 was added to the formulation. Both polyethylene glycol levels attempted were at 4.0% w/w (4% of the tablet weight). Due to the same problem, this trial was terminated, and no dissolution experiments were performed with this formulation.

The final replacement experiment removed the stearic acid and replaced it with the water soluble lubricant sodium stearyl fumerate. The formulation produced in this trial was as follows:

Stearic Acid Replaced with Sodium Stearyl Fumerate

| Ingredients | Mg/Tablet | % of Composition |
|---|---|---|
| Potassium Oxaprozin | 677.9 mg | 82.7% |
| Pregelatinized Starch | 17.4 mg | 2.1% |
| Microcrystalline Cellulose | 104.4 mg | 12.7% |
| Silicon Dioxide | 4.0 mg | 0.5% |
| Sodium Stearyl Fumerate | 16.3 mg | 2.0% |
|  | 820.0 mg | 100.0% |

The level of sodium stearyl fumerate used was 2.0% w/w (2% of the tablet weight). The force of compression of the tablet machine had to be increased slightly to avoid sticking, but the tablet weights and flow of the formulation through the machine were good.

Dissolution Data
(Mean Dissolution Data, n = 6)

|  |  | 10 Min | 15 Min | 20 Min | 30 Min | 45 Min | 60 Min |
|---|---|---|---|---|---|---|---|
| Sodium lauryl Sulfate | Conc. | 76.3% | 93.9% | 99.9% | 99.9% | 100.1% | 99.8% |
|  | Std Dev | 2.265 | 1.690 | 1.072 | 1.080 | 1.004 | 0.995 |
| Sodium Stearyl Fumerate | Conc. | 75.7% | 94.1% | 101.1% | 101.6% | 102.0% | 102.1% |
|  | Std Dev | 2.570 | 2.249 | 1.962 | 1.869 | 1.703 | 1.756 |

The results of dissolution testing showed that, for the sodium lauryl sulfate and sodium stearyl fumerate replacements, the dissolution was enhanced. Both replacement experiments showed greater than 99.9% of tablets made of these formulations dissolving at the thirty minute interval.

EXAMPLE 10

Excipient Elimination

In this experiment, tablets were made using only potassium oxaprozin.

Potassium oxaprozin (the active) was weighed and fed into the die cavity manually. The tablet press was manually turned by the hand wheel. The active was compressed on 0.3261×0.7480" capsule shaped tooling to the point that a tablet was formed. The active stuck to the upper and lower punches initially but with increased force of compression a tablet that did not stick was produced. The manual weighing and die filling was continued as well as turning the tablet machine by the handwheel until approximately 70 tablets were produced. The tablets produced were submitted to the lab for dissolution testing. Tablets also were evaluated for physical characteristics of weight variation, thickness, hardness, and disintegration.

The tablets exhibited good weight variation, and held thickness well. The hardness was very low (1.3 kp ave.). The disintegration times were very fast (4 to 5 minutes).

| Dissolution Data (Mean Dissolution Data, n = 6) | | | | | | |
|---|---|---|---|---|---|---|
| | 10 Min | 15 Min | 20 Min | 30 Min | 45 Min | 60 Min |
| Concentration | 99.9% | 99.8% | 99.9% | 99.9% | 100.0% | 100.0% |
| Standard Deviation | 0.7 | 0.7 | 0.7 | 0.8 | 0.8 | 0.7 |

The conclusion that can be drawn from this experiment is that the tablet formulation which employed only the active potassium oxaprozin resulted in the formation of a tablet with an acceptable dissolution profile.

EXAMPLE 11

Maximum Stearic Acid Determination

The following experiments were conducted to determine the maximum amount of stearic acid that could be used as a lubricant in the current formula for potassium oxaprozin, without adversely affecting dissolution.

The maximum amount of stearic acid that can be used in a formulation containing potassium oxaprozin was determined in the following manner. Small batches were mixed in a V blender and then compressed on a rotary tablet press. The resulting tablets were tested for disintegration and the disintegration times were used as an indicator of whether the tablets might pass dissolution. The only difference in the formulations was the percentage of stearic acid utilized. The levels of stearic acid used were: 5.7, 10, 15, 17.5, and 20% w/w.

| Ingredients | Mg/Tablet | % Composition |
|---|---|---|
| Stearic Acid 5.7% | | |
| Potassium Oxaprozin | 678.0 mg | 94.3% |
| Stearic Acid | 41.0 mg | 5.7% |
| Total | 719.0 mg | 100.00% |
| Stearic Acid 10.0% | | |
| Potassium Oxaprozin | 678.0 mg | 90.0% |
| Stearic Acid | 75.0 mg | 10.0% |
| Total | 753.0 mg | 100.00% |
| Stearic Acid 15.0% | | |
| Potassium Oxaprozin | 678.0 mg | 85.0% |
| Stearic Acid | 120.0 mg | 15.0% |
| Total | 798.0 mg | 100.00% |
| Stearic Acid 17.5% | | |
| Potassium Oxaprozin | 678.0 mg | 82.5% |
| Stearic Acid | 144.0 mg | 17.5% |
| Total | 822.0 mg | 100.00% |
| Stearic Acid 20.0% | | |
| Potassium Oxaprozin | 678.0 mg | 80.0% |
| Stearic Acid | 170.0 mg | 20.0% |
| Total | 848.0 mg | 100.00% |

The disintegration times for the runs were:

| | | |
|---|---|---|
| Stearic Acid | 5.7% | 10–11 Minutes |
| Stearic Acid | 10.0% | 13–15 Minutes |
| Stearic Acid | 15.0% | 22–24 Minutes |
| Stearic Acid | 17.5% | 24–28 Minutes |
| Stearic Acid | 20.0% | 36–39 Minutes |

Based on the disintegration times for the various formulations, the 17.5% and 20% stearic acid formulations were submitted to the laboratory for dissolution testing.

| Dissolution Data (Mean Dissolution Data, n = 6) | | | | | | |
|---|---|---|---|---|---|---|
| | 10 Min | 15 Min | 20 Min | 30 Min | 45 Min | 60 Min |
| 17.5% Stearic Acid | | | | | | |
| Concentration | 34.9% | 47.1% | 58.0% | 77.0% | 96.8% | 101.3% |
| Standard Deviation | 1.0 | 1.2 | 1.2 | 1.0 | 1.7 | 4.2 |
| 20.0% Stearic Acid | | | | | | |
| Concentration | 28.7% | 39.0% | 48.3% | 64.3% | 84.0% | 97.2% |
| Standard Deviation | 1.2 | 1.3 | 1.5 | 1.8 | 2.6 | 1.9 |

The conclusion that can be drawn from the above experiment is that, the maximum amount of stearic acid that can be utilized in the formulation of a tablet with an acceptable dissolution profile is slightly greater than 17.5% but less than 20.0%.

EXAMPLE 12

Binder Maximum Concentration Experiments

The following experiments were conducted to determine the maximum amount of pregelatinized corn starch that could be used as a binder in the current formula for potassium oxaprozin, without adversely affecting dissolution.

All of the trials were manufactured in the same manner utilizing the same equipment. The ingredients we granulated in the Fuji Vertical Granulator, dried in a force air oven, and tableted on the Kilian rotary tablet press. The only difference was the percentage of starch utilized in each of the formulations. The levels of pregelatinized corn starch were: 5, 10, 12.5, 15 and 30% W/W. After the tablets had been compressed they were submitted to the lab for dissolution testing.

The individual formulas are as follows:

| Ingredients | Mg/Tablet | % of Composition |
|---|---|---|
| Starch 5% | | |
| Potassium Oxaprozin | 678.0 mg | 93.0% |
| Pregelatinized Corn Starch | 36.5 mg | 5.0% |
| Stearic Acid | 14.5 mg | 2.0% |
| | 729.0 mg | 100.0% |
| Starch 10% | | |
| Potassium Oxaprozin | 678.0 mg | 88.0% |
| Pregelatinized Corn Starch | 77.0 mg | 10.0% |
| Stearic Acid | 15.0 mg | 2.0% |
| | 770.0 mg | 100.0% |
| Starch 12.5% | | |
| Potassium Oxaprozin | 678.0 mg | 85.5% |
| Pregelatinized Corn Starch | 99.0 mg | 12.5% |
| Stearic Acid | 16.0 mg | 2.0% |
| | 793.0 mg | 100.0% |
| Starch 15% | | |
| Potassium Oxaprozin | 678.0 mg | 83.0% |
| Pregelatinized Corn Starch | 122.0 mg | 15.0% |
| Stearic Acid | 16.0 mg | 2.0% |
| | 816.0 mg | 100.0% |
| Starch 30% | | |
| Potassium Oxaprozin | 678.0 mg | 68.0% |
| Pregelatinized Corn Starch | 299.0 mg | 30.0% |
| Stearic Acid | 20.0 mg | 2.0% |
| | 997.0 mg | 100.0% |

Dissolution Data
(Mean Dissolution Data, % Dissolved/RSD)

| | | 10 Min | 15 Min | 20 Min | 30 Min | 45 Min | 60 Min |
|---|---|---|---|---|---|---|---|
| 5% Starch | Conc. | 85.1% | 97.7% | 98.4% | 98.5% | 98.4% | 98.6% |
| | Std Dev | 1.6 | 0.4 | 0.8 | 0.7 | 0.9 | 0.8 |
| 10% Starch | Conc. | 80.0% | 97.6% | 98.6% | 98.7% | 98.8% | 98.8% |
| | Std Dev | 16.6 | 1.2 | 0.9 | 1.0 | 1.0 | 0.8 |
| 12.5% Starch | Conc. | 81.3% | 96.2% | 98.4% | 98.6% | 98.4% | 98.6% |
| | Std Dev | 4.8 | 2.1 | 1.1 | 1.1 | 1.2 | 1.3 |
| 15% Starch | Conc. | 81.6% | 96.2% | 99.8% | 99.8% | 99.7% | 99.9% |
| | Std Dev | 5.0 | 2.2 | 1.0 | 1.3 | 1.0 | 1.2 |
| 30% Starch | Conc. | 64.9% | 83.9% | 95.4% | 99.7% | 99.7% | 99.7% |
| | Std Dev | 4.0 | 3.2 | 2.5 | 1.4 | 1.3 | 1.5 |

The results of dissolution testing show that the level of pregelatinized corn starch, even at 30%, does not adversely affect the dissolution. It is on this basis that it can be predicted that any level of pregelatinized corn starch can be utilized and that it will most likely not affect the dissolution.

The foregoing examples are provided to enable one of ordinary skill in the art to practice the present invention. These examples are merely illustrative, however, and should not be read as limiting the scope of the invention as it is claimed in the appended claims.

(7) Description of Clinical Trials (A) Bioavailability Studies

Pharmacokinetic, clinical bioavailability studies on the oxaprozin potassium salt formulation described in Example 2 are described below, and included single and multiple-dose studies comparing plasma concentrations of total and unbound oxaprozin obtained with Daypro® (acid form of oxaprozin), and with the oxaprozin potassium salt described in Example 2.

Single Dose Study

A twelve day, open label, randomized, parallel, single dose study was conducted in 36 healthy subjects (12 per treatment) ages 19–44 years (27 males and 9 females) at Evanston Hospital in Evanston, Ill. in March and April of 1995 to evaluate the rate of absorption (how quickly it goes from the stomach into systemic circulation, in terms of $C_{max}$) and bioavailability (the percentage of the formulation which becomes absorbed from the gastrointestinal tract) of oxaprozin in fasted subjects from single 1200 mg oral doses (two 600 mg caplets) of three formulations of oxaprozin as: (1) 100% acid (Daypro®); (2) 60%/40% potassium salt/acid combination; and (3) 100% oxaprozin potassium salt formulation described in Example 2. Patients each received one single dose of one of these three formulations. Blood samples for oxaprozin analysis were obtained at predetermined intervals for a ten day period after dosing. Plasma oxaprozin parameters assessed were AUC, AUC o-∞, $C_{max}$, $T_{max}$, MRT and $T_{1/2}$ for both unbound oxaprozin and total oxaprozin (unbound oxaprozin plus oxaprozin bound to the plasma protein albumin). (NSAIDs as a class exhibit extensive plasma protein binding, mostly to albumin.)

Plasma concentrations of both total and unbound oxaprozin were plotted against time for each subject. In addition, mean plasma concentrations of total and unbound oxaprozin were plotted against time for each treatment group.

From each plasma concentration-time curve, the following pharmacokinetic parameters were calculated for both total and unbound oxaprozin:

$C_{max}$, the maximum observed total oxaprozin concentration;

$T_{max}$, the actual time of the maximum observed total oxaprozin concentration;

$AUC_{(0-T)}$, the area under the oxaprozin plasma concentration-time curve estimated using the linear trapezoidal method:

$$AUC_{(0-T)} = \sum_{i=1}^{n-1} \frac{C_{i+1} + C_i}{2} (t_{i+1} - t_i)$$

where T=240 hours for total oxaprozin and 48 hours for unbound oxaprozin, $c_i$ is the oxaprozin concentration of the ith plasma sample, $t_i$ is the actual time of the ith plasma sample, and n is the number of non-missing oxaprozin samples up to T hours posttreatment;

$AUC_{(0-\infty)}$, the area under the oxaprozin plasma concentration-time curve from time=0 to infinity, computed as follows:

$$AUC_{(0-\infty)} = AUC_{(0-T_{LQC})} + \frac{LQC}{\beta}$$

where $T_{LQC}$ is the time when the last quantified concentration was observed, LQC is the last quantifiable oxaprozin plasma concentration, and $\beta$ is the terminal elimination rate constant estimated as the negative of the slope of the simple linear regression line of loge (oxaprozin plasma concentration) versus time (the number of time points used in the regression line is determined after examination of the shape of the oxaprozin plasma concentration-time curve);

$MRT_{(0-\infty)}$, the mean residence time for the oxaprozin plasma concentration-time curve from time=0 to infinity, computed as follows:

$$MRT_{(0-\infty)} = \frac{AUMC_{(0-\infty)}}{AUC_{(0-\infty)}}$$

where $AUMC_{(0-\infty)}$ is the area under the curve of a plot of the product of oxaprozin plasma concentration and time versus time from zero to infinity, known as the area under the (first) moment curve, and computed as follows:

$$AUMC_{(0-\infty)} = AUMC_{(0-T_{LQC})} + \frac{T_{LQC}LQC}{\beta} + \frac{LQC}{\beta^2}$$

$$AUMC_{(0-t^2)} = \sum_{i=1}^{n-1} \frac{t_{i+1}C_{i+1} + t_i C_i}{2} (t_{i+1} - t_i)$$

$T_{1/2}$: terminal elimination half life for oxaprozin plasma levels, computed as $T_{1/2} = \log_e 2/\beta$.

For both total and unbound oxaprozin the following pharmacokinetic parameters were compared across the three groups: AUC, MRT, $C_{max}$, $T_{max}$, and $T_{1/2}$. In these comparisons, oxaprozin acid is referred to as the reference formulation and the other two formulations as the test formulations. AUC, MRT and $C_{max}$ were $\log_e$ transformed prior to the analysis. For each loge transformed parameter, a 90% confidence interval was computed for the difference (test−reference) between the arithmetic means. The endpoints of that interval were exponentiated to obtain an approximate 90% confidence interval for the ratio of the corresponding geometric means (test/reference).

The results of the above study with respect to Daypro® and the 100% potassium oxaprozin salt formulation are summarized in Table 1 hereinbelow.

Compared to Daypro®, the 100% salt formulation demonstrated a more rapid rate of absorption. Peak plasma concentrations ($C_{max}$) of total and unbound oxaprozin with the 100% potassium oxaprozin salt treatment were increased by 26% and 49%, respectively. Plasma concentrations with the salt formulation were less variable [AUC(0-240) for total drug: CV=14% (salt) as compared with 26% (Daypro®)]. This means that the plasma concentrations of drug in patients should be more predictable for patients who took the oxaprozin potassium salt formulation than for patients who took Daypro®.

Multiple Dose Study

An open label, randomized, parallel, multiple dose study in 40 (36 completed the study) healthy subjects (12 per treatment) was conducted to evaluate the bioavailability of total and unbound oxaprozin from multiple 1200 mg doses of oxaprozin given once daily for eight days as oxaprozin acid (Daypro®) tablet, the 60%/40% salt/acid mixture or the 100% potassium oxaprozin salt formulation described in Example 2. Total and unbound plasma concentrations of oxaprozin were measured by high performance liquid chromatography (HPLC) from blood samples taken at several time periods over a 24 hour period after the dose on days 1, 5 and 8 and from predose (trough) samples taken on days 3, 4 and 7.

Plasma concentrations of total and unbound oxaprozin were plotted against time for each subject for Study Days 1, 5, and 8. In addition, mean plasma concentrations of total and unbound oxaprozin were plotted against time for each treatment group. The concentrations of total and unbound oxaprozin were summarized at each time point by treatments.

From each plasma concentration-time curve, the following pharmacokinetic parameters were calculated for both total and unbound oxaprozin for Study Days, 1, 5 and 8:

$C_{max}$: the maximum observed total oxaprozin concentration, $C_{min}$: the pre-dose oxaprozin plasma concentration, $T_{max}$: the actual time of the maximum observed total oxaprozin concentration, and $AUC_(0-24)$: the area under the oxaprozin plasma concentration-time curve estimated using the linear trapezoidal method:

$$AUC_{(0-24)} = \sum_{i=1}^{n-1} \frac{C_{i+1} + C_i}{2} (t_{i+1} - t_i)$$

where $C_i$ is the oxaprozin concentration of the $i$th plasma sample, $t_i$ is the actual time of the $i$th plasma sample, and n is the number of non-missing oxaprozin samples up to 24 hours posttreatment.

In addition, the following pharmacokinetic parameter was calculated for both total and unbound oxaprozin for Study Days 5 and 8:

$(C_{max-Cmin})/C_{min}$

If the pre-dose plasma value was missing at Study Day 1, a zero value was used to calculate the pharmacokinetic parameters. If the pre-dose plasma value was missing at Study Day 5 or Study Day 8, the pre-dose plasma value of the previous study day was carried forward to calculate the pharmacokinetic parameters.

Pharmacokinetic parameters for both total and unbound oxaprozin were summarized for the three treatment groups for Study Days 1, 5 and 8 using the standard summary statistics, AUC, $C_{max}$, $C_{min}$ and $T_{max}$.

The ratios of Study Day 8 AUC to Study Day 1 AUC were compared across the three groups using a one way analysis of variance model for both total and unbound oxaprozin. The ratios were log transformed prior to the analysis.

Within each treatment, the following parameters were compared between Study Day 5 and Study Day 8 using a 90% confidence interval for the ratio of the means:

AUC, $C_{max}$, $C_{min}$, $T_{max}$ and $(C_{max}-C_{min})/C_{min}$.

In each of these comparisons, Study Day 5 was referred to as the reference and Study Day 8 was referred to as the test.

The between treatment comparisons were made for AUC, $C_{max}$ and $T_{max}$ at Study Day 1 and for AUC, $C_{max}$, $C_{min}$, $T_{max}$ and $(C_{max}-C_{min})/C_{min}$ at Study Day 8 using a 90% confidence interval for the ratio of the means. These comparisons were made for oxaprozin 100% salt (test) vs. oxaprozin 100% acid (reference) and for oxaprozin 60% salt/40% acid (test) vs. oxaprozin 100% acid (reference).

In both within-treatment and between-treatment comparisons, AUC, $C_{max}$, $C_{min}$ and $(C_{max}-C_{min})/C_{min}$ were log transformed prior to the analysis. For each log transformed parameter, a 90% confidence interval was computed for the difference (test–reference) between the arithmetic means. The endpoints of that interval were exponentiated to obtain an approximate 90% confidence interval for the ratio of the corresponding geometric means (test/reference).

For the untransformed parameters, each 90% confidence interval was obtained as hereafter described. An approximate 90% confidence interval was first obtained for the difference (test–reference) between the arithmetic means. The required approximate 90% interval for the ratio of arithmetic means was obtained by dividing the endpoints of that interval by the arithmetic mean of the reference and adding 1 to each result.

Parameters obtained from the different formulations (or different Study Days) were considered equivalent if the calculated 90% confidence interval was entirely contained within (0.8, 1.25) for the log transformed parameters and within (0.8, 1.2) for the untransformed parameters.

The results of the multiple dose study are summarized in Table 2. Comparison of the steady-state pharmacokinetic parameters for either total or unbound oxaprozin with Daypro® and with the potassium oxaprozin formulation described in Example 2 gave similar results when either day 5 or day 8 concentration values were used. For this reason, data for day 5 only are presented in this discussion.

Less between-subject variability in the plasma concentrations of oxaprozin potassium salt formulation subjects when compared with Daypro® subjects was also seen at steady state [% CV for AUC(0-24) total oxaprozin=15% (salt) as compared with 36% (Daypro®)]. Comparison of steady-state parameters on day 5 indicated that relative to Daypro®, the salt gave 12% and 4% higher $C_{max}$ and AUC(0-24), respectively, for the total drug. For the unbound drug there was a 23% increase in $C_{max}$ and no increase in the AUC(0-24) (Table 2).

Conclusions

The results of single-dose and multiple-dose bioavailability studies described above demonstrate the following:

(1) With the potassium oxaprozin salt formulation described in Example 2, the absorption rate of oxaprozin was faster and less variable than that with the Daypro® tablets.

(2) After equivalent 1200 mg doses administered as Daypro® or the potassium oxaprozin salt formulation, exposure to total or free oxaprozin at steady state with the salt did not exceed those with oxaprozin acid by more than 10%.

(3) The potassium oxaprozin salt formulation demonstrated less variability than that of the Daypro® tablets or salt/acid combination tablets.)

TABLE 1A

Single-dose Noncompartmental Pharmacokinetic Parameters of Total and Unbound Oxaprozin

| Single-dose Pharmacokinetic Parameter | Daypro ® 1200 mg N = 12[a] | Potassium Oxaprozin 1200 mg N = 12[a] | Daypro ® 1800 mg N = 35[b] |
|---|---|---|---|
| Total Oxaprozin; Mean (% CV) | | | |
| AUC(0–240) (hr · mcg/ml) | 8708 (26%) | 8649 (14%) | 10290 (24%) |
| AUC(0–∞) (hr · mcg/ml) | 9420 (28%) | 9079 (16%) | —* |
| MRT (hr) | 169 (16%) | 149 (14%) | — |
| $C_{max}$ (mcg/ml) | 125 (15%) | 157 (15%) | 175 (16%) |
| $t_{max}$ (hr) | 3.20 (49%) | 2.04 (43%) | 3.09 (27%) |
| t½ β (hr) | 62.8 (33%) | 52.6 (19%) | — |
| Unbound Oxaprozin; Mean (% CV) | | | |
| AUC(0–48) (hr · ng/ml) | 5999 (44%) | 6977 (26%) | 11258 (30%) |
| AUC(0–∞) (hr · ng/ml) | 9153 (49%) | 8931 (21%) | — |
| MRT (hr) | 71.0 (13%) | 59.9 (11%) | — |
| $C_{max}$ (ng/ml) | 268 (54%) | 401 (40%) | 573 (33%) |
| $t_{max}$ (hr) | 3.00 (32%) | 2.83 (107%)[c] | 3.11 (34%) |
| t½ β (hr) | 30.7 (23%) | 22.6 (19%) | — |

*—means not calculated
[a] Day 5 data from the first multiple dose study described above.
[b] Day 5 data from the second multiple dose study described above.

TABLE 2A

Steady-state Noncompartmental Pharmacokinetic Parameters of Total and Unbound Oxaprozin Total oxaprozin; Mean (% CV)

| Steady-state Pharmacokinetic Parameter | Daypro ® 1200 mg QD N = 12[a] | Potassium Oxaprozin 1200 mg QD N = 12[a] | Daypro ® 1800 mg QD N = 24[b] | |
|---|---|---|---|---|
| AUC(0–24) (hr · mcg/ml) | 4125 (36%) | 4289 (15%) | 5143 (23%) | |
| $C_{max}$ (mcg/ml) | 23.6 (27%) | 266 (10%) | 295 (18%) | |
| $t_{max}$ (hr) | | 3.1 (80%) | 1.7 (59%) | 3.2 (39%) |

Unbound Oxaprozin; Mean (% CV)

| Steady-state Pharmacokinetic Parameter | Daypro ® 1200 mg QD N = 12[a] | Potassium K salt 1200 mg QD N = 12[a] | Daypro ® 1800 mg QD N = 24[b] | |
|---|---|---|---|---|
| AUC(0–24) (hr · ng/ml) | 14808 (74%) | 14794 (30%) | 36274 (51%) | |
| $C_{max}$ (ng/ml) | 1163 (62%) | 1435 (27%) | 2600 (39%) | |
| $t_{max}$ (hr) | | 2.9 (65%) | 1.5 (46%) | 3.2 (48%) |

[a]Day 5 data from the first multiple dose study described above.
[b]Day 5 data from the second multiple dose study described above.

(B) Analgesia Studies

Two oxaprozin potassium salt formulations were evaluated in a single-blind, placebo controlled, single dose analgesia study in patients requiring treatment of postsurgical dental pain resulting from tooth extractions. The two formulations evaluated were the 100% oxaprozin potassium salt formulation described in Example 2 and a combination tablet containing the same ingredients, and percentages thereof, with the exception that, for the active ingredient, a combination of 60% oxaprozin potassium and 40% oxaprozin acid was employed. Daypro® was included in the study as a reference product. Nuprin (Ibuprofen, Bristol-Myers, New York, N.Y.) was included in the study as a positive control, and placebo was included in the study as a negative control. The objective of the study was to obtain analgesia data for the two potassium formulations.

The study was a single-blind, single dose, parallel group design in which 282 patients were randomized into the following five treatment groups:

(1) Daypro® 1200 mg single dose (2 600 mg tablets)—57 Patients
(2) 100% oxaprozin potassium salt formulation described in Example 2, 1200 mg single dose (2 600 mg tablets)—58 Patients
(3) Oxaprozin potassium/oxaprozin acid 60%/40% combination 1200 mg single dose (2 600 mg tablets)—56 Patients
(4) Nuprin 400 mg single dose (2 200 mg tablets)—56 Patients
(5) Placebo (2 tablets)—55 Patients The following different efficacy variables were measured and compared: (1) pain intensity difference (PID) using both a categorical scale (Tables 1 and 2) and a VAS (visual analog scale) (Tables 3 and 4); (2) pain relief assessed using a categorical scale (Tables 5 and 6); (3) a categorical pain relief and pain intensity difference combination measure (PRID) (Tables 7 and 8); and (4) percent of patients experiencing 50% pain relief (Tables 9 and 10). All of the variables were assessed at baseline (time just prior to taking the study medication, and which is after the patient has experienced severe to moderate pain), and at 0.25, 0.5, 0.75, 1.0, 1.5, 2, 3, 4, 5, 6, 7, and 8 hours. The visual analog scale expresses the magnitude of pain in mm on a printed 100 mm line which goes from no pain at 0 mm to worst pain at 100 mm. The categorical scale expresses pain intensity difference (PID) as a score on a 4-point scale which is as follows: 0=none, 1=slight, 2=moderate and 3=severe.

Results for the statistical analyses performed on the different efficacy variables described above are presented in Tables 1–10 hereinbelow.

In Tables 1–4, pain intensity difference (PID) measures the change in pain from baseline. It is calculated as follows: (Pain Score Baseline) minus (Pain Score at Time H). Positive values indicate diminished pain (pain relief from baseline). SPID1 is the sum of each patient's pain intensity difference (PID) at time 0.25, 0.50, 0.75 and 1.00 hour. Tmax(PID) is the time when a patient's pain intensity difference (PID) reaches its maximum value (maximum pain relief) over the 8 hour time interval.

In Tables 5 and 6, the Pain Relief scale expresses pain relief as a score on a 4-point scale which is as follows: 0=none, 1=a little, 2=some, 3=a lot, 4=complete. The pain relief scores are used to calculate pain relief means for each time point. Larger values indicate better pain relief. TOTPAR1 is the sum of each patient's Pain Relief Scores at time 0.25, 0.50, 0.75 and 1.00 hour. Tmax(PAR) is the time when Pain Relief Scores reaches its maximum value over the 8 hour time interval.

In Tables 7 and 8, PRID is the sum PID (categorical scale) and Pain Relief Scores for each time point. Large values indicate better Pain Relief. SPRID1 is the sum of each patient's PRID at time 0.25, 0.50, 0.75 and 1.00 hour. Tmax(PRID) is the time when PRID reaches its maximum value (maximum pain relief) over the 8 hour time interval.

In Tables 9 and 10, the number of hours with 50% pain relieved is calculated as the sum of all time intervals the patient experienced 50% pain relief. The censoring value (a standard number employed to place into the equation for patients who did not experience 50% pain relief at 3 hours, and who took rescue medication) was 8.1. (Rescue medication is any pain relieving medication, such as ibuprofen or vicodin). '****' indicates that the time a patient first experienced at least 50% pain relief exceeds 8 hours. The 95% confidence interval for median is calculated using the non-parametric sign test, as is described in R. Brookmeyer et al., "A Confidence Interval for the Median Survival Time," *Biometrics*, 38, 29–41 (1982), which is incorporated herein by reference.

In Table 10, the P-Values (probability value of statistical significance between the two values being compared) with respect to the number of hours with 50% pain relieved are from the SAS PROC GLM contrast statements (standard statistical computer programs known by those of skill in the art, which are available from SAS Institute, Inc., Cary, N.C., and which are incorporated herein by reference). The P-Values with respect to the first time 50% pain relief was experienced was from the LOG RANK test which is described in R. G. Miller, *Survival Analysis* (John Wiley & Sons, New York, N.Y., 1981), which is incorporated herein by reference.

The 100% oxaprozin potassium tablet described in Example 2 demonstrated a statistically significantly faster onset of action than oxaprozin acid and was numerically better than the oxaprozin potassium/oxaprozin acid combination tablet in every efficacy parameter.

No statistically significant difference was noted between oxaprozin potassium and oxaprozin acid or oxaprozin potassium and the oxaprozin potassium/oxaprozin acid combination within the first hour for either PID measurement ($p \geq 0.055$). However, there were statistically significant differences between the oxaprozin potassium salt formulation described in Example 2 as compared with DAYPRO® within the first hour for pain relief scores (starting at 0.5 hours, probability (p)=0.017), sum of pain intensity difference and pain relief (starting at 0.5 hours, p=0.042) and percent of patients experiencing at least 50% pain relief (starting at 0.75 hours, p=0.043). The oxaprozin potassium salt formulation described in Example 2 was the most efficacious, considering performance over the first hour and time to maximum value for the efficacy variables.

Conclusions

The oxaprozin potassium salt formulation described in Example 2 provides a statistically significantly faster onset of action compared to DAYPRO® with the difference occurring at 0.5 to 0.75 hours following dosing. In addition, the oxaprozin potassium salt formulation described in Example 2 was numerically better than the oxaprozin potassium/oxaprozin acid for all efficacy parameters for the first hour following dosing. (The onset of analgesic action is defined as the time that the efficacy parameter for the oxaprozin potassium salt formulation becomes significantly different from placebo, and occurs within (prior to) the 1 hour post treatment time period.)

TABLE 1

PAIN INTENSITY DIFFERENCE (PID)

Categorical Scale

Mean (Standard Deviation)

| Hours | PLACEBO (n = 55) | DAYPRO ® 1200 MG (n = 57) | OXAPROZIN SALT 1200 MG (n = 58) | OXAPROZIN SALT/ACID 1200 MG (n = 56) | NUPRIN 400 MG (n = 56) |
|---|---|---|---|---|---|
| Baseline | 2.20 (0.40) | 2.18 (0.38) | 2.17 (0.38) | 2.14 (0.35) | 2.13 (0.33) |
| 0.25 | 0.00 (0.47) | −0.09 (0.34) | 0.05 (0.35) | −0.05 (0.30) | 0.11 (0.45) |
| 0.50 | −0.02 (0.56) | −0.04 (0.42) | 0.07 (0.53) | 0.04 (0.50) | 0.34 (0.58) |
| 0.75 | −0.02 (0.68) | 0.11 (0.59) | 0.26 (0.71) | 0.09 (0.58) | 0.70 (0.76) |
| 1.00 | −0.02 (0.73) | 0.18 (0.68) | 0.36 (0.77) | 0.27 (0.70) | 0.95 (0.75) |
| 1.50 | −0.16 (0.81) | 0.42 (0.84) | 0.60 (0.86) | 0.57 (0.85) | 1.16 (0.83) |
| 2.00 | −0.18 (0.82) | 0.47 (0.87) | 0.71 (0.92) | 0.68 (0.86) | 1.20 (0.84) |
| 3.00 | −0.22 (0.79) | 0.65 (1.04) | 0.71 (0.97) | 0.77 (0.89) | 1.27 (0.86) |
| 4.00 | −0.15 (0.93) | 0.67 (1.06) | 0.66 (1.00) | 0.79 (0.95) | 1.29 (0.87) |
| 5.00 | −0.15 (0.93) | 0.67 (1.07) | 0.66 (1.04) | 0.73 (0.90) | 1.02 (0.88) |
| 6.00 | −0.13 (0.98) | 0.67 (1.06) | 0.60 (0.99) | 0.75 (0.96) | 0.91 (0.88) |
| 7.00 | −0.15 (0.93) | 0.65 (1.04) | 0.57 (0.99) | 0.77 (0.99) | 0.79 (0.91) |
| 8.00 | −0.15 (0.93) | 0.68 (1.07) | 0.53 (0.98) | 0.77 (1.01) | 0.71 (0.87) |
| SPID1 | −0.05 (2.19) | 0.16 (1.75) | 0.74 (2.00) | 0.34 (1.71) | 2.09 (2.18) |
| Tmax (PID) | 0.74 (1.24) | 1.52 (1.80) | 1.31 (1.27) | 1.87 (1.90) | 1.37 (1.10) |

TABLE 2

PAIN INTENSITY DIFFERENCE (PID)
Categorical Scale
P-Values from SAS PROC GLM Contrast Statements

| Hours | OXAPROZIN SALT 1200 MG | vs. | DAYPRO ® 1200 MG | OXAPROZIN SALT/ACID 1200 MG | vs. | DAYPRO ® 1200 MG |
|---|---|---|---|---|---|---|
| Baseline | 0.965 | | | 0.642 | | |
| 0.25 | 0.055 | | | 0.640 | | |
| 0.50 | 0.285 | | | 0.471 | | |
| 0.75 | 0.220 | | | 0.899 | | |
| 1.00 | 0.170 | | | 0.500 | | |
| SPID1 | 0.114 | | | 0.626 | | |
| Tmax (PID) | 0.460 | | | 0.213 | | |

TABLE 3

PAIN INTENSITY DIFFERENCE (PID)
Visual Analog Scale
Mean (Standard Deviation)

| Hours | PLACEBO (n = 55) | DAYPRO ® 1200 MG (n = 57) | OXAPROZIN SALT 1200 MG (n = 58) | OXAPROZIN SALT/ACID 1200 MG (n = 56) | NUPRIN 400 MG (n = 56) |
|---|---|---|---|---|---|
| Baseline | 59.42 (12.30) | 57.51 (13.86) | 54.24 (14.49) | 58.51 (10.93) | 54.88 (13.05) |
| 0.25 | −1.27 (11.69) | −2.77 (10.08) | −0.33 (9.41) | −2.91 (11.01) | 1.88 (12.67) |
| 0.50 | −1.78 (15.26) | −3.95 (11.68) | 0.41 (14.55) | −1.11 (15.48) | 9.32 (18.75) |
| 0.75 | −1.27 (19.59) | −1.09 (17.68) | 4.07 (22.16) | 2.55 (18.68) | 19.55 (22.21) |
| 1.00 | −2.00 (21.77) | 2.05 (19.55) | 8.21 (25.40) | 8.11 (21.18) | 25.84 (22.57) |
| 1.50 | −5.78 (24.56) | 10.54 (26.44) | 14.93 (27.66) | 17.22 (25.15) | 32.88 (24.05) |
| 2.00 | −7.40 (24.72) | 12.58 (28.29) | 17.34 (29.63) | 21.71 (26.91) | 34.39 (25.78) |
| 3.00 | −7.64 (25.26) | 16.56 (31.61) | 17.93 (31.93) | 25.18 (30.29) | 36.98 (26.33) |
| 4.00 | −6.40 (27.91) | 18.26 (33.18) | 17.17 (32.84) | 25.98 (31.67) | 36.52 (26.95) |
| 5.00 | −6.38 (27.91) | 18.56 (33.70) | 15.72 (32.95) | 26.13 (31.75) | 31.61 (27.42) |
| 6.00 | −6.20 (28.37) | 18.05 (33.43) | 15.52 (32.68) | 25.76 (32.57) | 27.91 (27.81) |
| 7.00 | −6.33 (28.14) | 18.39 (33.77) | 14.79 (33.16) | 25.45 (32.48) | 24.18 (28.85) |
| 8.00 | −6.16 (28.41) | 18.95 (34.36) | 14.48 (33.20) | 25.02 (32.87) | 23.38 (28.52) |
| SPID1 | −6.33 (64.24) | −5.75 (53.98) | 12.36 (65.85) | 6.64 (59.15) | 56.59 (69.24) |
| Tmax | 1.22 (1.65) | 2.35 (2.54) | 2.20 (2.00) | 3.46 (2.61) | 2.37 (1.88) |

TABLE 4

PAIN INTENSITY DIFFERENCE (PID)
Visual Analog Scale
P-Values from SAS PROC GLM Contrast Statements

| Hours | OXAPROZIN SALT 1200 MG | vs. | DAYPRO ® 1200 MG | OXAPROZIN SALT/ACID 1200 MG | vs. | DAYPRO ® 1200 MG |
|---|---|---|---|---|---|---|
| Baseline | 0.179 | | | 0.685 | | |
| 0.25 | 0.235 | | | 0.948 | | |
| 0.50 | 0.128 | | | 0.327 | | |
| 0.75 | 0.171 | | | 0.341 | | |
| 1.00 | 0.138 | | | 0.150 | | |
| SPID1 | 0.123 | | | 0.297 | | |
| Tmax (PID) | 0.707 | | | 0.007 | | |

TABLE 5

PAIN RELIEF SCORES (PAR)
Mean (Standard Deviation)

| Hours | PLACEBO (n = 55) | DAYPRO ® 1200 MG (n = 57) | OXAPROZIN SALT 1200 MG (n = 58) | OXAPROZIN SALT/ACID 1200 MG (n = 56) | NUPRIN 400 MG (n = 56) |
|---|---|---|---|---|---|
| 0.25 | 0.25 (0.55) | 0.19 (0.52) | 0.34 (0.55) | 0.18 (0.51) | 0.34 (0.84) |
| 0.50 | 0.44 (0.69) | 0.32 (0.57) | 0.66 (0.71) | 0.50 (0.69) | 0.98 (1.05) |
| 0.75 | 0.58 (0.83) | 0.54 (0.78) | 1.02 (1.03) | 0.80 (0.72) | 1.70 (1.25) |
| 1.00 | 0.67 (0.90) | 0.72 (0.82) | 1.29 (1.26) | 1.02 (0.88) | 2.05 (1.24) |
| 1.50 | 0.60 (0.99) | 1.32 (1.31) | 1.67 (1.44) | 1.52 (1.10) | 2.48 (1.32) |
| 2.00 | 0.62 (1.03) | 1.49 (1.42) | 1.79 (1.50) | 1.82 (1.21) | 2.63 (1.32) |
| 3.00 | 0.62 (1.06) | 1.77 (1.66) | 1.90 (1.56) | 2.02 (1.36) | 2.79 (1.37) |
| 4.00 | 0.71 (1.27) | 1.86 (1.69) | 1.84 (1.62) | 2.05 (1.43) | 2.79 (1.44) |
| 5.00 | 0.71 (1.27) | 1.88 (1.72) | 1.84 (1.67) | 2.04 (1.37) | 2.48 (1.48) |
| 6.00 | 0.75 (1.34) | 1.84 (1.69) | 1.81 (1.63) | 2.05 (1.42) | 2.32 (1.47) |
| 7.00 | 0.71 (1.27) | 1.82 (1.68) | 1.76 (1.65) | 2.09 (1.47) | 2.14 (1.52) |
| 8.00 | 0.71 (1.27) | 1.86 (1.72) | 1.67 (1.63) | 2.11 (1.49) | 2.07 (1.46) |
| TOTPAR1 | 1.95 (2.69) | 1.77 (2.40) | 3.31 (3.11) | 2.50 (2.37) | 5.07 (3.83) |
| Tmax (PAR) | 0.91 (1.41) | 1.87 (1.91) | 1.69 (1.52) | 2.40 (2.13) | 1.54 (1.13) |

TABLE 6

PAIN RELIEF SCORES (PAR)
P-Values from SAS PROC GLM Contrast Statements

| Hours | OXAPROZIN SALT 1200 MG | vs. | DAYPRO ® 1200 MG | OXAPROZIN SALT/ACID 1200 MG | vs. | DAYPRO ® 1200 MG |
|---|---|---|---|---|---|---|
| 0.25 | | 0.179 | | | 0.899 | |
| 0.50 | | 0.017 | | | 0.199 | |
| 0.75 | | 0.008 | | | 0.145 | |
| 1.00 | | 0.003 | | | 0.128 | |
| TOTPAR1 | | 0.005 | | | 0.188 | |
| Tmax (PAR) | | 0.555 | | | 0.092 | |

TABLE 7

SUM OF PAIN INTENSITY DIFFERENCE AND PAIN RELIEF (PRID)
Mean (Standard Deviation)

| Hours | PLACEBO (n = 55) | DAYPRO ® 1200 MG (n = 57) | OXAPROZIN SALT 1200 MG (n = 58) | OXAPROZIN SALT/ACID 1200 MG (n = 56) | NUPRIN 400 MG (n = 56) |
|---|---|---|---|---|---|
| 0.25 | 0.25 (0.93) | 0.11 (0.72) | 0.40 (0.79) | 0.13 (0.69) | 0.45 (1.25) |
| 0.50 | 0.42 (1.13) | 0.28 (0.86) | 0.72 (1.09) | 0.54 (1.08) | 1.32 (1.56) |
| 0.75 | 0.56 (1.41) | 0.65 (1.27) | 1.28 (1.67) | 0.89 (1.20) | 2.39 (1.94) |
| 1.00 | 0.65 (1.54) | 0.89 (1.40) | 1.66 (1.96) | 1.29 (1.50) | 3.00 (1.93) |
| 1.50 | 0.44 (1.73) | 1.74 (2.09) | 2.28 (2.25) | 2.09 (1.86) | 3.64 (2.07) |
| 2.00 | 0.44 (1.77) | 1.96 (2.23) | 2.50 (2.36) | 2.50 (2.00) | 3.82 (2.10) |
| 3.00 | 0.40 (1.77) | 2.42 (2.66) | 2.60 (2.48) | 2.79 (2.20) | 4.05 (2.18) |
| 4.00 | 0.56 (2.14) | 2.53 (2.71) | 2.50 (2.58) | 2.84 (2.33) | 4.07 (2.26) |
| 5.00 | 0.56 (2.14) | 2.54 (2.76) | 2.50 (2.66) | 2.77 (2.23) | 3.50 (2.30) |
| 6.00 | 0.62 (2.26) | 2.51 (2.71) | 2.41 (2.57) | 2.80 (2.33) | 3.23 (2.29) |
| 7.00 | 0.56 (2.14) | 2.47 (2.68) | 2.33 (2.59) | 2.86 (2.42) | 2.93 (2.37) |
| 8.00 | 0.56 (2.14) | 2.54 (2.75) | 2.21 (2.55) | 2.88 (2.45) | 2.79 (2.26) |
| SPRID1 | 1.89 (4.57) | 1.93 (3.84) | 4.05 (4.88) | 2.84 (3.78) | 7.16 (5.84) |
| Tmax (PRID) | 0.91 (1.41) | 1.87 (1.91) | 1.71 (1.51) | 2.40 (2.13) | 1.55 (1.13) |

TABLE 8

SUM OF PAIN INTENSITY DIFFERENCE AND PAIN RELIEF (PRID)
P-Values from SAS PROC GLM Contrast Statements

| Hours | OXAPROZIN SALT 1200 MG | vs. | DAYPRO ® 1200 MG | OXAPROZIN SALT/ACID 1200 MG | vs. | DAYPRO ® 1200 MG |
|---|---|---|---|---|---|---|
| 0.25 | | 0.083 | | | 0.907 | |
| 0.50 | | 0.042 | | | 0.246 | |
| 0.75 | | 0.029 | | | 0.397 | |
| 1.00 | | 0.016 | | | 0.218 | |
| SPRID1 | | 0.015 | | | 0.299 | |
| Tmax (PRID) | | 0.602 | | | 0.091 | |

TABLE 9

Percent of Patients Experiencing At Least 50% Pain Relief

| Hours | PLACEBO (n = 55) | DAYPRO ® 1200 MG (n = 57) | OXAPROZIN SALT 1200 MG (n = 58) | OXAPROZIN SALT/ACID 1200 MG (n = 56) | NUPRIN 400 MG (n = 56) |
|---|---|---|---|---|---|
| 0.25 | 5.5 | 1.8 | 3.4 | 1.8 | 5.4 |
| 0.50 | 7.3 | 1.8 | 8.6 | 7.1 | 21.4 |
| 0.75 | 10.9 | 8.8 | 24.1 | 10.7 | 46.4 |
| 1.00 | 14.5 | 10.5 | 37.9 | 25.0 | 60.7 |
| 1.50 | 16.4 | 36.8 | 51.7 | 46.4 | 73.2 |
| 2.00 | 16.4 | 43.9 | 55.2 | 55.4 | 78.6 |
| 3.00 | 16.4 | 47.4 | 58.6 | 60.7 | 78.6 |
| 4.00 | 16.4 | 49.1 | 51.7 | 57.1 | 75.0 |
| 5.00 | 16.4 | 47.4 | 50.0 | 58.9 | 67.9 |
| 6.00 | 16.4 | 49.1 | 50.0 | 58.9 | 62.5 |
| 7.00 | 16.4 | 47.4 | 48.3 | 57.1 | 55.4 |
| 8.00 | 16.4 | 47.4 | 46.6 | 57.1 | 55.4 |
| Mean (SD) Number of Hours With 50% Pain Relief | 1.24 (2.74) | 3.34 (3.41) | 3.77 (3.44) | 4.12 (3.33) | 5.04 (2.97) |
| Time First Experienced 50% Pain Relieved Tmax (PAR) Median | **** | 6:00 | 1:30 | 2:00 | 1:00 |
| (LCL, UCL) | (****, ****) | (2:00, ****) | (1:00, ****) | (1:30, 3:00) | (0:45, 1:30) |

TABLE 10

Percent of Patients Experiencing At Least 50% Pain Relief
P-Values From Fishers Exact Test

| Hours | OXAPROZIN SALT 1200 MG | vs. | DAYPRO ® 1200 MG | OXAPROZIN SALT/ACID 1200 MG | vs. | DAYPRO ® 1200 MG |
|---|---|---|---|---|---|---|
| 0.25 | | 1.009 | | | 1.000 | |
| 0.50 | | 0.206 | | | 0.206 | |
| 0.75 | | 0.043 | | | 0.762 | |
| 1.00 | | <0.001 | | | 0.051 | |
| Number of Hours with 50% Pain Relieved | | 0.467 | | | 0.194 | |
| Time First Experienced 50% Pain Relief | | 0.083 | | | 0.068 | |

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active ingredient selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

To the extent any component of the formulation herein can be categorized in more than one of the groupings of components, the amount of such component in the aggregate shall be within the range of such component as described with respect to its use as either a binder or lubricant.

What is claimed is:

1. A pharmaceutical composition in a solid dosage form comprising potassium, sodium or Tris salt of oxaprozin as an active agent, wherein the pharmaceutical composition contains less than 1% (w/w) magnesium stearate and wherein about 75% of the active agent in said solid dosage form becomes dissolved in 1000 ml of pH 7.4 phosphate buffer media at 37° C. with paddle stirring at 75 rpm within about 30 minutes.

2. The pharmaceutical composition of claim 1, wherein the active agent is the potassium salt of oxaprozin.

3. The pharmaceutical composition of claim 1, wherein the active agent is the sodium salt of oxaprozin.

4. The pharmaceutical composition of claim 1, wherein the active agent is the Tris salt of oxaprozin.

5. The pharmaceutical composition of any one of claims 1–4, wherein the active agent is from about 37.14% to about 100% by weight of the total composition.

6. The pharmaceutical composition of claim 1, wherein the pharmaceutical composition contains less than 2% (w/w) methylcellulose.

7. The pharmaceutical composition of claim 1, wherein said composition is substantially free of metallic stearates.

8. The pharmaceutical composition of claim 1, wherein the solid dosage form is a tablet, pill or caplet.

9. A pharmaceutical composition in a solid dosage form comprising (i) a potassium, sodium or Tris salt of oxaprozin as an active agent, and (ii) a lubricant selected from the group consisting of water-insoluble lubricants and water-soluble lubricants, wherein about 75% of the active agent in said solid dosage form becomes dissolved in 1000 ml of pH 7.4 phosphate buffer media at 37° C. with paddle stirring at 75 rpm within about 30 minutes.

10. The pharmaceutical composition of claim 9, wherein the active agent is from about 37.14% to about 100% by weight of the total composition.

11. The pharmaceutical composition of claim 8, wherein the lubricant is from about 0.25% to about 20% by weight of the total composition.

12. The pharmaceutical composition of claim 9, wherein the pharmaceutical composition contains less than 1% (w/w) magnesium stearate.

13. The pharmaceutical composition of claim 9, wherein the pharmaceutical composition is substantially free of metallic stearates.

14. The pharmaceutical composition of claim 9, wherein the pharmaceutical composition contains less than 2% (w/w) methylcellulose.

15. The pharmaceutical composition of claim 11, wherein the solid dosage form is a tablet, pill or caplet.

16. The pharmaceutical composition of claim 9, wherein the water-insoluble lubricant is selected from the group consisting of calcium stearate, zinc stearate, stearic acid, hydrogenated vegetable oil and talc.

17. The pharmaceutical composition of claim 9, wherein the water-soluble lubricant is sodium lauryl sulfate or sodium stearyl fumarate.

18. The pharmaceutical composition of claim 9, further comprising a binder.

19. The pharmaceutical composition of claim 18, wherein the binder is from about 0.25% to about 30% by weight of the total composition.

20. The pharmaceutical composition of claim 19, wherein said binder is selected from the group consisting of cornstarch, pregelatinized cornstarch, sucrose, polyvinylpyrrolidone, methylcellulose, sodium carboxymethyl cellulose and ethylcellulose.

21. The pharmaceutical composition of claim 18, further comprising a filler.

22. The pharmaceutical composition of claim 21, wherein said filler is microcrystalline cellulose.

23. A pharmaceutical composition in a solid dosage form comprising (i) a potassium, sodium or Tris salt of oxaprozin as an active agent in an amount from about 70% to about 90% by weight of the composition; (ii) stearic acid in an amount from about 1% to about 4% by weight of the composition; (iii) pregelatinized corn starch in an amount of about 0.25% to about 25% by weight of the composition and (iv) optionally microcrystalline cellulose in an amount from about 0% to about 27% by weight of the composition, wherein about 75% of the active agent in said solid dosage form becomes dissolved in 1000 ml of pH 7.4 phosphate buffer media at 37° C. with paddle stirring at 75 rpm within about 30 minutes.

24. The pharmaceutical composition of claim 23, wherein said active agent is potassium oxaprozin.

25. The pharmaceutical composition of claim 24, wherein said microcrystalline cellulose is present.

26. The pharmaceutical composition of claim 23, wherein the pharmaceutical composition contains less than 1% (w/w) magnesium stearate.

27. The pharmaceutical composition of claim 23, wherein the pharmaceutical composition is substantially free of metallic stearates.

28. The pharmaceutical composition of claim 23, wherein the pharmaceutical composition contains less than 2% w/w methylcellulose.

29. A method of eliminating or ameliorating pain in a mammal in need of such treatment comprising the step of administering to said mammal an effective amount of a pharmaceutical composition in a solid dosage form comprising potassium, sodium or Tris salt of oxaprozin as an active agent, wherein about 75% of the active agent in said solid dosage form becomes dissolved in 1000 ml of pH 7.4 phosphate buffer at 37° C. with paddle stirring at 75 rpm within about 30 minutes.

30. The method of claim 29, wherein the active agent is from about 37.14% to about 100% by weight of the total composition.

31. The method of claim 29, wherein the solid dosage form is a tablet, pill or caplet.

32. A method of treating inflammation or inflammation associated disorders in a mammal in need of such treatment comprising the step of administering to said mammal an effective amount of a pharmaceutical composition in solid dosage form comprising potassium, sodium or Tris salt of oxaprozin as an active agent, wherein about 75% of the active agent in said solid dosage form becomes dissolved in 1,000 ml of pH 7.4 phosphate buffer media at 37°C. with paddle stirring at 75 rpm within about 30 minutes.

33. The method of claim 32, wherein the active agent is from about 37.14% to about 100% by weight of the total composition.

34. The method of claim 32, wherein the solid dosage form is a tablet, pill or caplet.

35. The pharmaceutical composition of any of claims 1, 9 or 23, wherein about 95% of the active agent in said solid dosage form becomes dissolved in said phosphate buffer media within about 30 minutes.

36. The method of claim 29, wherein about 95% of the active agent in said solid dosage form becomes dissolved in said phosphate buffer media within about 30 minutes.

* * * * *

UNITED STATES PATENT AND TRADEMARK OFFICE
CERTIFICATE OF CORRECTION

PATENT NO. : 6,030,643
DATED : February 29, 2000
INVENTOR(S) : MARK E. ADAMS ET AL.

It is certified that error appears in the above-identified patent and that said Letters Patent is hereby corrected as shown below:

COLUMN 11:

Line 1, "than" should read --then--.

COLUMN 15:

Line 22, "of" should be deleted.

COLUMN 25:

Line 20, "Japan.)" should read --Japan).--.

COLUMN 31:

Line 54, "Ouantities" should read --Quantities--.

COLUMN 55:

Line 9, "loge" should read --$\log_e$--;
Line 38, "T ½." should read --$T_½$.--; and
Line 42, "loge" should read --$\log_e$--.

COLUMN 56:

Line 30, "$AUC_{(}0-24)$:" should read --$AUC_{(0-24)}$:--; and
Line 46, "$(C_{max-cmin})/C_{min}$" should read --$(C_{max}-C_{min})/C_{min}$--.

COLUMN 58:

Table 1A, "t½β(hr)" (both occurrences) should read --$t_½β(hr)$--.

UNITED STATES PATENT AND TRADEMARK OFFICE
CERTIFICATE OF CORRECTION

PATENT NO. : 6,030,643

DATED : February 29, 2000

INVENTOR(S) : MARK E. ADAMS ET AL.

It is certified that error appears in the above-identified patent and that said Letters Patent is hereby corrected as shown below:

COLUMN 59:

Table 2A, in the 2nd column, "23.6 (27%)" should read --236 (27%)--.

Signed and Sealed this

Tenth Day of April, 2001

Attest:

NICHOLAS P. GODICI

Attesting Officer      Acting Director of the United States Patent and Trademark Office